United States Patent
Schardl et al.

(10) Patent No.: US 11,021,760 B2
(45) Date of Patent: Jun. 1, 2021

(54) FUNGAL CHROMOSOME-END KNOCKOFF STRATEGY

(71) Applicant: University of Kentucky Research Foundation, Lexington, KY (US)

(72) Inventors: Christopher L. Schardl, Lexington, KY (US); Simona Florea, Lexington, KY (US); Mark L. Farman, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 557 days.

(21) Appl. No.: 15/610,860

(22) Filed: Jun. 1, 2017

(65) Prior Publication Data

US 2017/0349899 A1    Dec. 7, 2017

Related U.S. Application Data

(60) Provisional application No. 62/346,728, filed on Jun. 7, 2016.

(51) Int. Cl.
*C12Q 1/6895* (2018.01)
*C12N 15/52* (2006.01)

(52) U.S. Cl.
CPC ............ *C12Q 1/6895* (2013.01); *C12N 15/52* (2013.01)

(58) Field of Classification Search
None
See application file for complete search history.

(56) References Cited

U.S. PATENT DOCUMENTS

2012/0047609 A1 *   2/2012   Yu .......................... C12N 15/82
800/320.1

OTHER PUBLICATIONS

Young et al (Toxins, 2015, 7: 1273-1302) (Year: 2015).*
Panaccione et al (J. Argic. Food Chem., 2006, 54: 4582-4587) (Year: 2006).*
Parish et al (J. Anim. Sci., 2003, 81(11): 2856-2868) (Year: 2003).*
Lucia et al (Bioinformatics Trends and Methodologies, Ed. Dr. Mahmood A. Mahdavi, 2011, Chapter 19: Basidiomycetes Telomeres, pp. 393-424) (Year: 2011).*
GenBank KC989608 (published online Aug. 2013; see appended sequence alignment) (Year: 2013).*
Livak KJ, Schmittgen TD: Analysis of relative gene expression data using real-time quantitative PCR and the 2-ΔΔCT method. Methods 2001, 25:402-408.
Malinowski DP, Belesky DP: Ecological importance of *Neotyphodium* spp. grass endophytes in agroecosystems. Grassland Science 2006, 52:1-14.
Nagabhyru P, Dinkins RD, Wood CL, Bacon CW, Schardl CL: Tall fescue endophyte effects on tolerance to water-deficit stress. BMC Plant Biology 2013, 13:127. doi: 110.1186/1471-2229-1113-1127.
Nicholson MJ, Koulman A, Monahan BJ, Pritchard BL, Payne GA, Scott B: Identification of two aflatrem biosynthetic gene loci in Aspergillus flavus and metabolic engineering of Penicillium paxilli to elucidate their function. Appl Environ Microbiol 2009, 75:7469-7481.
Pan J, Bhardwaj M, Nagabhyru P, Grossman RB, Schardl CL: Enzymes from fungal and plant origin required for chemical diversification of insecticidal loline alkaloids in grass-Epichloë symbiota. PLoS One 2014, 9:e115590. doi: 115510.111371/journal.pone. 0115590.
Panaccione DG, Johnson RD, Wang JH, Young CA, Damrongkool P, Scott B, Schardl CL: Elimination of ergovaline from a grass-Neotyphodium endophyte symbiosis by genetic modification of the endophyte. Proc Natl Acad Sci USA 2001, 98:12820-12825.
Panaccione DG, Tapper BA, Lane GA, Davies E, Fraser K: Biochemical outcome of blocking the ergot alkaloid pathway of a grass endophyte. J Agric Food Chem 2003, 51:6429-6437.
Panaccione DG, Ryan KL, Schardl CL, Florea S: Analysis and modification of ergot alkaloid profiles in fungi. Meth Enzymol 2012, 515:267-290.
Qi X, Li Y, Honda S, Hoffmann S, Marz M, Mosig A, Podlevsky JD, Stadler PF, Selker EU, Chen JJ-L: The common ancestral core of vertebrate and fungal telomerase RNAs. Nucl Acids Res 2013, 41:450-462.
Ryan KL, Moore CT, Panaccione DG: Partial reconstruction of the ergot alkaloid pathway by heterologous gene expression in Aspergillus nidulans. Toxins (Basel) 2013, 5:445-455.
Ryan KL, Akhmedov NG, Panaccione DG: Identification and structural elucidation of ergotryptamine, a new ergot alkaloid produced by genetically modified Aspergillus nidulans and natural isolates of Epichloë species. J Agric Food Chem 2015, 63:61-67.
Schardl CL: The Epichloae, Symbionts of the Grass Subfamily Pooideae. Ann. Missouri Bot. Gard. 97: 646-665 2010.
Schardl CL, et al.: Plant-symbiotic fungi as chemical engineers: multi-genome analysis of the Clavicipitaceae reveals dynamics of alkaloid loci. PLoS Genet 2013, 9:e1003323.
Schardl CL, Young CA, Pan J, Florea S, Takach JE, Panaccione DG, Farman ML, Webb JS, Jaromczyk J, Charlton ND, Nagabhyru P, Chen L, Shi C, Leuchtmann A: Currencies of mutualisms: sources of alkaloid genes in vertically transmitted epichloae. Toxins (Basel) 2013, 5:1064-1088.
Siegel MR, Johnson MC, Varney DR, Nesmith WC, Buckner RC, Bush LP, Burrus PB, II., Jones TA, Boling JA: A fungal endophyte in tall fescue: incidence and dissemination. Phytopathology 1984, 74:932-937.
Smith CA, Woloshuk CP, Robertson D, Payne GA: Silencing of the aflatoxin gene cluster in a diploid strain of Aspergillus flavus is suppressed by ectopic aflR expression. Genetics 2007, 176:2077-2086.

(Continued)

*Primary Examiner* — Stephen Uyeno
(74) *Attorney, Agent, or Firm* — Stites & Harbison PLLC; Mandy Wilson Decker

(57) ABSTRACT

Non-toxigenic fungal strains, and methods of making and use thereof, are provided and have utility as endophytes in forage crops, and as strains that can outcompete toxigenic strains in forage and food crops.

4 Claims, 5 Drawing Sheets
Specification includes a Sequence Listing.

(56) References Cited

OTHER PUBLICATIONS

Spiering MJ, Faulkner JR, Zhang D-X, Machado C, Grossman RB, Schardl CL: Role of the LolP cytochrome P450 monooxygenase in loline alkaloid biosynthesis. Fungal Genet Biol 2008, 45:1307-1314.
Spiering MJ, Davies E, Tapper BA, Schmid J, Lane GA: Simplified extraction of ergovaline and peramine for analysis of tissue distribution in endophyte-infected grass tillers. J Agric Food Chem 2002, 50:5856-5862.
Takach JE, Young CA: Alkaloid genotype diversity of tall fescue endophytes. Crop Sci 2014, 54:667-678.
Timper P, Gates RN, Bouton JH: Response of *Pratylenchus* spp. in tall fescue infected with different strains of the fungal endophyte Neotyphodium coenophialum. Nematology 2005, 7:105-110.
Tsai HF, Siegel MR, Schardl CL: Transformation of Acremonium coenophialum, a protective fungal symbiont of the grass Festuca arundinacea. Curr Genet 1992, 22:399-406.
Watanabe H, Somei M, Sekihara S-I, Nakagawa K, Yamada F: Dopamine receptor stimulating effects of chanoclavine analogues, tricyclic ergot alkaloids, in the brain. The Japanese Journal of Pharmacology 1987, 45:501-506.
Watson RH, McCann MA, Parish JA, Hoveland CS, Thompson FN, Bouton JH: Productivity of cow-calf pairs grazing tall fescue pastures infected with either the wild-type endophyte or a nonergot alkaloid-producing endophyte strain, AR542. J Animal Sci 2004, 82:3388-3393.
Young CA, Charlton ND, Takach JE, Swoboda GA, Trammell MA, Huhman DV, Hopkins AA: Characterization of Epichloë coenophiala within the US: are all tall fescue endophytes created equal? Frontiers in chemistry 2014, 2:95. doi: 10.3389/fchem.2014.00095.
An Z-Q, Siegel MR, Hollin W, Tsai H-F, Schmidt D, Schardl CL: Relationships among non-*Acremonium* sp. fungal endophytes in five grass species. Appl Environ Microbiol 1993, 59:1540-1548.
Blankenship JD, Spiering MJ, Wilkinson HH, Fannin FF, Bush LP, Schardl CL: Production of loline alkaloids by the grass endophyte, Neotyphodium uncinatum, in defined media. Phytochemistry 2001, 58:395-401.
Bouton JH, Latch GCM, Hill NS, Hoveland CS, McCann MA, Watson RH, Parish JA, Hawkins LL, Thompson FN: Reinfection of tall fescue cultivars with non-ergot alkaloid-producing endophytes. Agron J 2002, 94:567-574.
Cassady JM, Li GS, Spitzner EB, Floss HG, Clemens JA: Ergot alkaloids. Ergolines and related compounds as inhibitors of prolactin release. Journal of Medicinal Chemistry 1974, 17:300-307.
Chung KR, Hollin W, Siegel MR, Schardl CL: Genetics of host specificity in Epichloë typhina. Phytopathology 1997, 87:599-605.
Ehrlich KC: Non-aflatoxigenic Aspergillus flavus to prevent aflatoxin contamination in crops: advantages and limitations. Front Microbiol 2014, 5: 50. doi 10.3389/fmicb.2014.00050.
Ekanayake PN, Hand ML, Spangenberg GC, Forster JW, Guthridge KM: Genetic diversity and host specificity of fungal endophyte taxa in fescue pasture grasses. Crop Sci 2012, 52:2243-2252.
Florea S, Andreeva K, Machado C, Mirabito PM, Schardl CL: Elimination of marker genes from transformed filamentous fungi by unselected transient transfection with a Cre-expressing plasmid. Fungal Genet Biol 2009, 46:721-730.
Florea, S, Phillips, TD, Panaccione, DG, Farman, ML, Schardl, CL: Chromosome-End Knockoff Strategy to Reshape Alkaloid Profiles of a Fungal Endophyte. G3 2016, 6: 8, doi: 10.1534/g3.116.029686.
Florea S, Panaccione DG, Schardl CL: Ergot alkaloids of the family Clavicipitaceae. Phytopathology 2017, 107:504-518.
Latch GCM, Christensen MJ: Artificial infections of grasses with endophytes. Ann Appl Biol 1985, 107:17-24.
Joost Re: Conservation: erosion control, soil management and remediation, and effects on wildlife habitat. In: Tall Fescue for the Twenty-first Century. Edited by Fribourg HA, Hannaway DB, West CP. Madison, Wisconsin: American Society of Agronomy, Crop Science Society of America, Soil Science Society of America; 2009: 489-507.
Hopkins AA, Young CA, Butler TJ, Bouton JH: Registration of Texoma MaxQ II tall fescue. Journal of Plant Registration 2011, 5:14-18.
Hopkins AA, Young CA, Simpson WR, Panaccione DG, Mittal S, Bouton JH: Agronomic performance and lamb safety of tall fescue novel endophyte combinations in the south central USA. Crop Sci 2010, 50:1552-1561.
Florea S, Schardl CL, Rollin W: Detection and isolation of Epichloë species, fungal endophytes of grasses. Current Protocols in Microbiology 2015, 38:19A.11.11-19A.11.24.

* cited by examiner

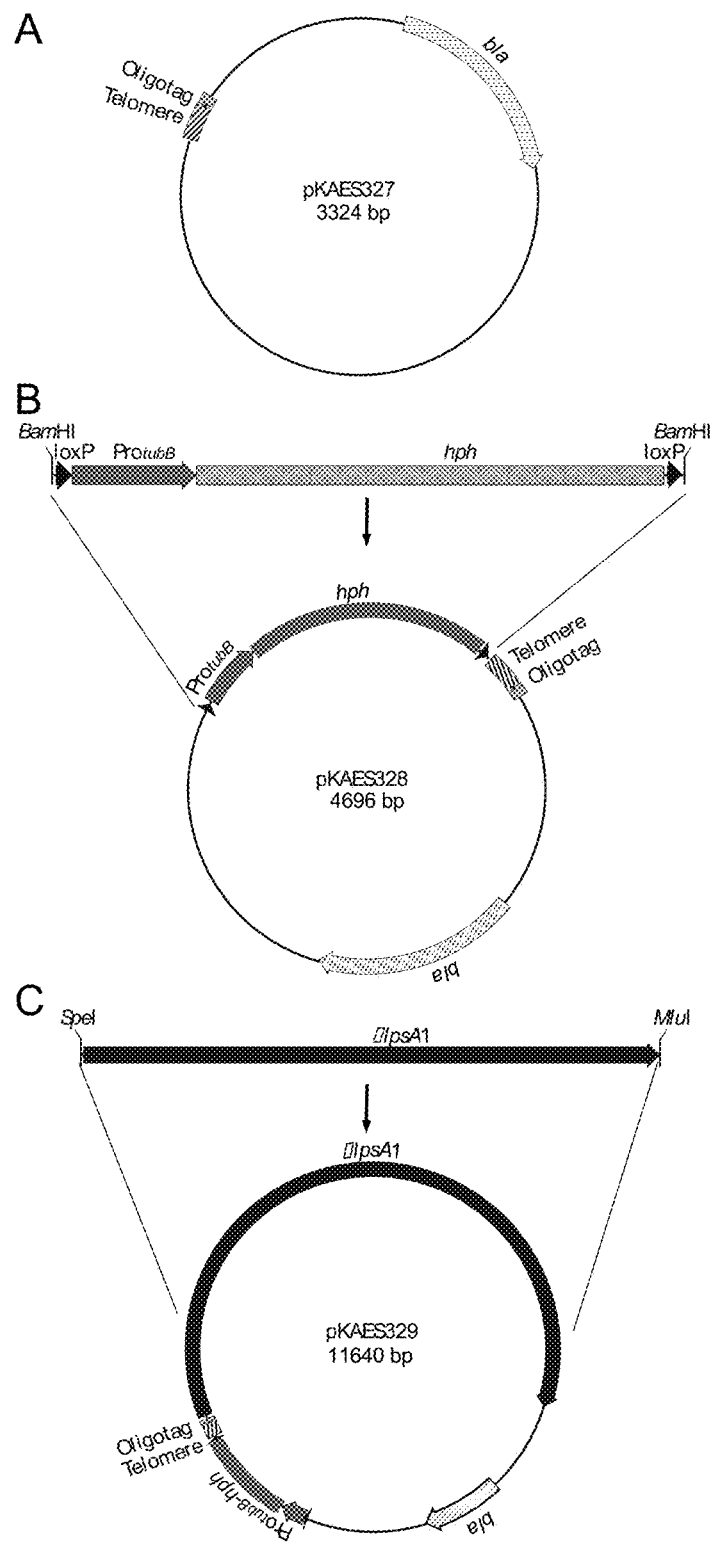
FIGS. 5A-C

FUNGAL CHROMOSOME-END KNOCKOFF STRATEGY

RELATED APPLICATIONS

This application claims priority from U.S. Provisional Application Ser. No. 62/346,728, filed Jun. 7, 2016, the entire disclosure of which is incorporated herein by this reference.

GOVERNMENT INTEREST

This invention was made with government support under Agriculture and Food Research Initiative grant 2012-67013-19384 awarded by the U.S. Department of Agriculture. The government has certain rights in the invention.

TECHNICAL FIELD

The presently-disclosed subject matter relates to compositions and methods for eliminating target genes in endophyte and other fungi strains.

INTRODUCTION

Tall fescue (Lolium arundinaceum=Schedonorus arundinaceus=Festuca arundinacea) is a perennial cool season grass widely used in the U.S. as a forage crop and for conservation and amenity purposes, due to its persistence, tolerance of drought and other stresses, resistance to pests and diseases, and excellent biomass yield [1]. Remarkably, these exceptional qualities are not strictly plant properties, but rather are significantly enhanced by the symbiotic, seed-transmitted fungus (endophyte), Epichloë coenophiala (=Neotyphodium coenophialum), which colonizes the above-ground parts of the host without causing harm to the plant. Furthermore, E. coenophiala cannot spread between neighboring plants, because the only means by which it transmits is by colonization of the seeds. Only plants symbiotic with the endophyte produce seeds with the endophyte, and they do so with extremely high efficiency [2]. Fitness benefits conferred by E. coenophiala to tall fescue plants include enhanced tillering, enhanced root growth, improved mineral uptake, increased drought tolerance and increased resistance to nematodes, diseases, and insect pests [3-6]. Like other Epichloë species, E. coenophiala produces a diverse array of alkaloids, specialized (secondary) metabolites that are not required by the fungus for growth and development, but instead protect against vertebrate or invertebrate herbivores [4]. Alkaloids such as lolines and peramine provide important protection from insects and perhaps nematodes. However, "common toxic endophyte" (CTE) strains of E. coenophiala also produce ergot alkaloids that, due to their effects on livestock, reduce the endophyte benefits for pasture and forage production [7].

According to their complexity, ergot alkaloids can be classified in three groups: clavine alkaloids, lysergic acid and its simple amides, and the notoriously toxic ergopeptines. Their biosynthesis proceeds through clavines to lysergic acid, then to the ergopeptines, such as ergovaline produced by E. coenophiala CTE strains. Ergot alkaloid synthesis (EAS) genes that encode the biosynthetic enzymes are clustered and located near the chromosome ends in sequenced genomes of Epichloë species. Those ends are protected by telomeres comprised of CCCTAA (SEQ ID NO: 31) tandem repeat units. In all, eleven EAS genes determine the pathway to ergovaline. However, E. coenophiala CTE strains have duplicate sets of ergot-alkaloid biosynthesis genes because E. coenophiala is a near triploid hybrid fungus, with genomes from three ancestral species [8]. Two of those ancestors contributed EAS loci, the third contributed a loline biosynthesis locus, and all three contributed peramine biosynthesis loci.

Intensive surveys of tall fescue in Europe and North Africa have identified some Moroccan ecotypes that lack ergot alkaloids, and certain non-toxic endophytes (NTE) have been cultured from those ecotypes and used to replace the CTE in order to produce novel cultivars. As expected, livestock performance on the novel cultivars is significantly better than on cultivars with their original CTE, and not significantly different than on tall fescue lacking endophyte. However, the NTE strains currently used for novel cultivars are derived from very different tall fescue ecotypes (summer dormant, Moroccan) than the northern (north European) ecotypes from which the summer active cultivars are derived, and in which the NTE are now being deployed. For that reason it is unsurprising that problems have been reported with the NTE strains in those cultivars. Some have exhibited less stability than the CTE strains or appear less effective against root-parasitic nematodes, a potentially important limitation to productivity and drought tolerance in the southeastern U.S. [6, 9, 12]. The reasons that Moroccan endophytes exhibit inconsistent anti-nematode activity are unknown, but conceivably relate to lower production of loline alkaloids, which are translocated to roots and can affect nematodes. Thus, although the search for existing NTE strains has been a commercial and agricultural success, they may not be the optimal choices for mixing and matching plant and symbiont strains for some U.S. pasturelands. Thus, there exists a need for NTE strains for novel cultivars in tall fescue ecotypes for U.S. pasturelands, and an approach for generating such NTE strains.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes methods for eliminating target genes in endophyte and other fungi strains, and the strains produced by the disclosed methods. In particular, a chromosome knock-off strategy is employed for elimination of toxin genes in the endophyte and other fungi strains.

The presently-disclosed subject matter, in one aspect, comprises an isolated nucleic acid molecule that includes a nucleic acid sequence of a selectable marker gene, a nucleic acid sequence of one or more telomere repeats, and a nucleic acid sequence including a variant or fragment of a wild type gene of an ergot alkaloid gene cluster.

In some embodiments, the nucleic acid sequence of a selectable marker gene where the marker gene is hph, neomycin phosphotransferase II gene, or a gene for resistance to phleomycin or bialophos.

In some embodiments, the nucleic acid sequence of a series of telomere repeats includes a sequence of a telomere repeat represented by one of SEQ ID NOs: 31-54 and the series includes about 3 to about 26 or more telomere repeats.

In some embodiments, the recombination sequence includes a variant or fragment of a wild type gene of an ergot alkaloid gene cluster selected from EAS1 or EAS2 in *Epichloë* species, an indole-diterpene gene cluster (IDT) in *Epichloë* or *Aspergillus* species and aflatoxin gene clusters. In some embodiments, the recombination sequence includes a gene fragment of lpsA1 (SEQ ID NO:3).

Vectors for use in modifying target genes in an endophyte or fungus are also disclosed herein. In some embodiments, the endophyte or fungus is selected from an *Epichloë* species, the species comprising *Epichloë festucae*, an *Epichloë festucae×Epichloë typhina* hybrid, or *Epichloë coenophiala* (formerly known as *Neotyphodium coenophialum*). In some embodiments, the vector includes the isolated nucleic acid sequences as disclosed herein. Kits including the vectors are also presently-disclosed.

Methods for eliminating target gene(s) in a fungus are also disclosed herein. In particular, methods for eliminating some or substantially all of a target gene located in a subterminal region of a chromosome in a fungus are provided. In some embodiments, the fungus is selected from an *Epichloë* species or *Aspergillus* species. The methods can comprise the steps of integrating a nucleic acid molecule as disclosed herein into the genome of the fungus by homologous recombination. In some embodiments, the target gene(s) are located in the subterminal region of a chromosome. In some embodiments, the homologous recombination replaces the target gene(s) in whole or in part. In some embodiments, the nucleic acid sequence of a series of telomere repeats will direct spontaneous loss of the nucleic acid sequence downstream of the recombinant telomere repeats, followed by stabilization of a new chromosome end including the recombinant telomere repeats. In some embodiments of the method, 70%, 75% or substantially all of the ergot alkaloid gene cluster is eliminated.

In some embodiments of the presently-disclosed methods, a portion of the ergot alkaloid gene cluster is eliminated sufficient to affect the expression of toxins in the fungus. In some embodiments, the expression of toxins in the fungus is reduced by at least 50%.

Endophyte and/or fungus strains produced by the methods disclosed herein are also provided. In some embodiments, the fungus strains are "knockoffs," [41] and include a recombinant nucleic acid sequence substantially lacking the target gene(s) and/or sequence, which in some embodiments, is an ergot alkaloid gene cluster. In some embodiments, the endophyte strain lacks a gene for dimethylallyltryptophan synthase (dmaW) or lysergylpeptide synthetase (lpsB). In some embodiments, the fungus strain is from *Aspergillus* species or from *Epichloë coenophiala* species. In some embodiments, the strain is selected from e19 (ATCC 90664), e4163, e7480, e7479 and e7575. In some embodiments, the fungus strain comprises a nucleic acid sequence of any one of SEQ ID NOS: 1-2. Synthetic combinations of the presently-disclosed endophyte strains with a fescue grass or perennial ryegrass are also disclosed herein.

BRIEF DESCRIPTION OF THE DRAWINGS

The novel features of the invention are set forth with particularity in the following description and in the appended claims. A better understanding of the features and advantages of the present invention will be obtained by reference to the following detailed description that sets forth illustrative embodiments, in which the principles of the invention(s) are used, and the accompanying drawings of which:

FIG. 5 includes schematics of A. plasmid pKAES327 where the telomere repeat array and adjacent oligotag were introduced into pKAES215 to produce pKAES327, which has a β-lactamase gene for selection in bacteria. B. pKAES328 where a loxP-flanked hygromycin phosphotransferase gene (hph), downstream of the promoter of *Epichloë typhina* tubB (gene for β-tubulin), was introduced into pKAES327 to give pKAES328. The loxP sites allow for Cre-mediated excision of the marker, a procedure that was not required in this study; and C. plasmid pKAES329 6944-bp fragment of the *E. coenophiala* e19 lpsA1 gene was introduced into pKAES328 to give pKAES329.

BRIEF DESCRIPTION OF THE SEQUENCE LISTING

Figure 1:
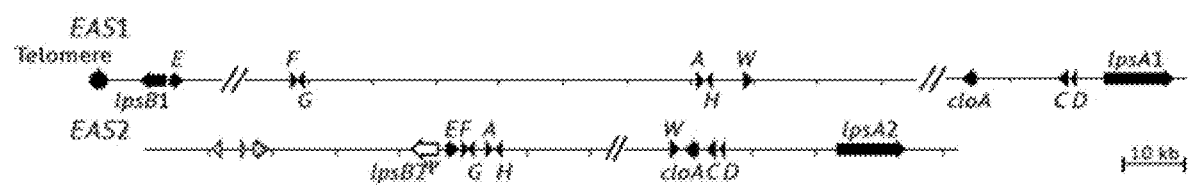
FIG. 1 depicts ergot alkaloid gene clusters EAS1 and EAS2 in *Epichloë coenophiala* e19. Names of eas genes and dmaW are abbreviated to their final capital letters. The lpsB2 pseudogene, which has an inactivating frame-shift mutation, is shown as an open-box arrow. Genome sequencing confirmed linkage of lpsB1 and easE1 to a telomere at the positions shown. Hash marks indicate gaps in the assembly, but the putative genes orders shown are similar to those in the genome assembly of *E. coenophiala* strain e4163.

SEQ ID NO: 1 is the nucleic acid sequence encoding the e7480 contig 32884.

SEQ ID NO: 2 is the nucleic acid sequence encoding the e7479 contig 40627.

SEQ ID NO: 3 is the nucleic acid sequence from lpsA1 used in pKAE329.

SEQ ID NO: 4 is the polynucleotide primer from the polylinkerDdeI and polylinkerSpeI.

SEQ ID NO: 5 is the polynucleotide primer lpsA1SpeI(f).

SEQ ID NO: 6 is the polynucleotide primer lpsA1MluI(r).

SEQ ID NO: 7 is the polynucleotide primer from the polylinkerDdeI.

SEQ ID NO: 8 is the polynucleotide primer from the polylinkerSpeI.

SEQ ID NO: 9 is the polynucleotide primer dmaWe19copy2(+)-1d.

SEQ ID NO: 10 is the polynucleotide primer dmaWe19copy2-(−)-5u.

SEQ ID NO: 11 is the polynucleotide primer dmaw1(f)

SEQ ID NO: 12 is the polynucleotide primer dmaWe19(−)-10

SEQ ID NO: 13 is the polynucleotide primer 144lpsBDraI(f2).

SEQ ID NO: 14 is the polynucleotide primer 144lpsB(r).

SEQ ID NO: 15 is the polynucleotide primer 215hphlpsB(f)

SEQ ID NO: 16 is the polynucleotide primer 215lpsBhph(r)

SEQ ID NO: 17 is the polynucleotide primer hph.3d.

SEQ ID NO: 18 is the polynucleotide primer hph.3u

SEQ ID NO: 19 is the polynucleotide primer RTq-E.c.easE(f)

SEQ ID NO: 20 is the polynucleotide primer RTq-E.c.easE(r)

SEQ ID NO: 21 is the polynucleotide primer RTq-E.c.easA(f)

SEQ ID NO: 22 is the polynucleotide primer RTq-E.c.easA(r)

SEQ ID NO: 23 is the polynucleotide primer RTq-E.c.easC(f).

SEQ ID NO: 24 is the polynucleotide primer RTq-E.c.easC(r).

SEQ ID NO: 25 is the polynucleotide primer RTq-E.c.easF(f).

SEQ ID NO: 26 is the polynucleotide primer RTq-E.c.easF(r).

SEQ ID NO: 27 is the polynucleotide primer RTq-E.c.easG(f).

SEQ ID NO: 28 is the polynucleotide primer RTq-E.c.easG(r).

SEQ II) NO: 29 is the polynucleotide primer oligoscreen (f).

SEQ ID NO: 30 is the polynucleotide primer lpsAoligo(r)

SEQ ID NO: 31 is the nucleic acid sequence CCCTAA which is a telomere repeat that can be repeated about 3 to about 26 times.

SEQ ID NO: 32 is the nucleic acid sequence CCCTAATGTTCA which is a telomere repeat that can be repeated about 3 to about 26 times.

SEQ ID NO: 33 is the nucleic acid sequence CCCTAAC which is a telomere repeat that can be repeated about 3 to about 26 times.

SEQ ID NO: 34 is the nucleic acid sequence CTAACC which is a telomere repeat that can be repeated about 3 to about 26 times.

SEQ ID NO: 35 is the nucleic acid sequence TAACCC which is a telomere repeat that can be repeated about 3 to about 26 times.

SEQ ID NO: 36 is the nucleic acid sequence AACCCT which is a telomere repeat that can be repeated about 3 to about 26 times.

SEQ ID NO: 37 is the nucleic acid sequence ACCCTA which is a telomere repeat that can be repeated about 3 to about 26 times.

SEQ ID NO: 38 is the nucleic acid sequence TAAGGG which is a telomere repeat that can be repeated about 3 to about 26 times.

SEQ ID NO: 39 is the nucleic acid sequence AAGGGT which is a telomere repeat that can be repeated about 3 to about 26 times.

SEQ ID NO: 40 is the nucleic acid sequence AGGGTA which is a telomere repeat that can be repeated about 3 to about 26 times.

SEQ ID NO: 41 is the nucleic acid sequence GGGTAA which is a telomere repeat that can be repeated about 3 to about 26 times.

SEQ ID NO: 42 is the nucleic acid sequence GGTAAG which is a telomere repeat that can be repeated about 3 to about 26 times.

SEQ ID NO: 43 is the nucleic acid sequence GTAAGG which is a telomere repeat that can be repeated about 3 to about 26 times.

SEQ ID NO: 44 is the nucleic acid sequence CCTAATGTTCAC which is a telomere repeat that can be repeated about 3 to about 26 times.

SEQ ID NO: 45 is the nucleic acid sequence CTAATGTTCACC which is a telomere repeat that can be repeated about 3 to about 26 times.

SEQ ID NO: 46 is the nucleic acid sequence TAATGTTCACCC which is a telomere repeat that can be repeated about 3 to about 26 times.

SEQ ID NO: 47 is the nucleic acid sequence AATGTTCACCCT which is a telomere repeat that can be repeated about 3 to about 26 times.

SEQ ID NO: 48 is the nucleic acid sequence ATGTTCACCCTA which is a telomere repeat that can be repeated about 3 to about 26 times.

SEQ ID NO: 49 is the nucleic acid sequence TGTTCACCCTAA which is a telomere repeat that can be repeated about 3 to about 26 times.

SEQ ID NO: 50 is the nucleic acid sequence GTTCACCCTAAT which is a telomere repeat that can be repeated about 3 to about 26 times.

SEQ ID NO: 51 is the nucleic acid sequence TTCACCCTAATG which is a telomere repeat that can be repeated about 3 to about 26 times.

SEQ ID NO: 52 is the nucleic acid sequence TCACCCTAATGT which is a telomere repeat that can be repeated about 3 to about 26 times.

SEQ ID NO: 53 is the nucleic acid sequence CACCCTAATGTT which is a telomere repeat that can be repeated about 3 to about 26 times.

SEQ ID NO: 54 is the nucleic acid sequence ACCCTAATGTTC which is a telomere repeat that can be repeated about 3 to about 26 times.

SEQ ID NO: 55 is a nucleic acid sequence canonical telomere repeat array of the scaffold of the e19 assembly (GenBank accession KC989609.1) downstream of lpsB1.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter meets some or all of the above-identified needs, as will become evident to those of ordinary skill in the art after a study of information provided in this document. To avoid excessive repetition, this Description does not list or suggest all possible combinations of such features.

Presented herein is a novel approach to generate non-toxic endophyte strains, based on the tendency for toxin genes to be located near chromosome ends [14]. This approach was also designed to abolish all exogenous genes including the selectable marker used in endophyte transformation. The approach was used to eliminate the telomere-associated EAS1 gene cluster from the genome of a Continental European *E. coenophiala* ecotype, and genome sequencing confirmed that the resulting ΔEAS1 strains lacked transgenes. These strains lack ergovaline, and may be suitable, therefore, for tall fescue pastures and forage.

The technique was tested on *Epichloë coenophiala*, a seed-transmissible symbiotic fungus (endophyte) of the important forage grass, tall fescue. The endophyte is necessary for maximal productivity and sustainability of this grass but can produce ergot alkaloids such as ergovaline, which are toxic to livestock. The gene arrangements are similar in several other *Epichloë* species. In most of the species, there is only a single gene cluster rather than the duplicate set of functional genes found in *E. coenophiala*. Thus, similar manipulations of other species, such as *Epichloë festucae*, which include endophytes of many fescue grasses and perennial ryegrass, or an *Epichloë festucae× typhina* hybrid also found in perennial ryegrass, are envisioned. Additionally, in some embodiments where elimination of the entire ergot alkaloid biosynthetic pathway is desired, a targeting plasmid can be designed to the centromeric side (that is, telomere distal side) of dmaW, the gene for the first step in the pathway. For *Epichloë* species generally, in some embodiments, the amino acid sequence of the EAS genes have at least 50% identity to the amino acid sequence of the EAS genes in *Epichloë coenophiala*, at least 60%, at least 70%, at least 80%, at least 90%, or at least 95% identity. *Aspergillus* species also contain toxin genes near chromosome ends and can be utilized with the currently disclosed methods. See, e.g., M J Nicholson et al. [15], and C A Smith et al. [16].

In some embodiments, an isolated nucleic acid molecule is provided including a nucleic acid sequence of a marker gene, a series telomere repeats and a recombination gene sequence comprising a variant or fragment of a wild type gene of an ergot alkaloid gene cluster or a sequence that has at least 50% identity to the sequence of any one of a wild type gene of an ergot alkaloid gene cluster. The variant or fragment of a wild type gene can contain at least one substitution and/or at least one deletion modification relative to the sequence.

In some embodiments, an isolated nucleic acid molecule is provided with a nucleic acid sequence comprising a nucleic acid sequence of a selectable marker gene selected from hph (GenBank accession No. X03615.1), neomycin phosphotransferase II gene (GenBank accession No. ACH99098.1), or gene for resistance to phleomycin (GenBank accession No. X52869.1) and/or bialophos (GenBank accession No. X05822.1); a series of telomere repeats selected from [CCCTAA]$_{3-26}$ which can be represented as [SEQ ID NO:31]$_{3-26}$; and [CCCTAATGTTCA]$_{3-26}$ which can be represented as [SEQ ID NO:32]$_{3-26}$ or a sequence of any one of SEQ ID NOs. 31-54 with about 3 to about 26 or more telomere repeats; and a recombination sequence comprising a variant or fragment of a wild type gene of an ergot alkaloid gene cluster selected from EAS1 [GenBank Accession Nos. KC989607, KC989608, and KC989609 for strain e19, and KC989569 for strain e4163] or EAS2 [GenBank Accession Nos. KC989610 and KC98961 I for strain e19, and KC989570 for strain e4163] in *Epichloë* species, an indole-diterpene gene cluster (IDT) in *Epichloë* or *Aspergillus* species [GenBank Accession No. AY559849.2] and aflatoxin gene clusters [e.g., GenBank Accession No. NW_002477243.1].

The *Aspergillus* species have telomere-associated genes for production of aflatoxin and cyclopiazonic acid. The methods disclosed herein can be used to eliminate aflatoxin genes and cyclopiazonic acid genes, and other toxin genes that are telomere-linked. Elimination of toxin genes in *Aspergillus* would be desirable, as indicated in Ehrlich KC (2014) Non-aflatoxigenic *Aspergillus flavus* to prevent aflatoxin contamination in crops: advantages and limitations. Front Microbiol 5: 50. doi 10.3389/fmicb.2014.00050

With regard to the marker gene, in some embodiments, the marker gene is a fungal-active hygromycin phosphotransferase gene (hph) selectable marker. Other selectable markers, such as other antibiotic resistance markers, auxotrophic complementation markers and substrate utilization markers can be used. For example, antibiotic resistance markers include genes for resistance to geneticin (GenBank accession No. ACH99098.1), phleomycin (GenBank accession No. X52869.1) or bialophos (GenBank accession No. X05822.1). An auxotrophic complementation marker can be, for example, the gene for orotidine-5'-phosphate decarboxylase, which is required for uracil biosynthesis. A substrate utilization marker can be, for example, a gene for acetamidase, which can confer the ability to grow using acetamide as a sole carbon source or nitrogen reductase.

The telomere repeat can depend on the fungus. In some embodiments, the telomere repeat comprises SEQ ID NO:31 CCCTAA, where the number of tandem repeats can range from 3-26. Different fungal species can have different telomere repeat units, such a SEQ ID NO:32 CCCTAATGTTCA in *Aspergillus oryzae*. See, e.g. Qi et al. *Nucl Acids Res* 2013, 41(1):450-462. In some embodiments, the telomere repeat can be selected from SEQ ID NOs: 31, 32, 33, 34, 35, 36, 37, 38, 39, 40, 41, 42, 43, 44, 45, 46, 47, 48, 49, 50, 51, 52, 53, and 54. The number of tandem repeats for the telomeres disclosed herein can range from 3 to 26 or more repeats.

Regarding gene clusters that can be targeted utilizing the methods of the present invention, in some embodiments the aflatoxin clusters in *Aspergillus* species or the ergot alkaloid clusters and indole-diterpene clusters in *Epichloë* species are targeted because of their location, and because of the use in agriculture. In some embodiments, the gene cluster from which the target gene(s) is selected is an ergot alkaloid gene cluster such as EAS1 [GenBank Accession Nos. KC989569 for e4163, and KC989609, KC989607 and KC989608 for e19], EAS2 [GenBank Accession Nos. KC989570 for e4163, and KC989611 and KC989610 for e19], an indole-diterpene (tremorgen) gene cluster (IDT), a cyclopiazonic acid gene cluster, or the aflatoxin gene cluster. However, the method is based on toxin genes located in the subterminal region of the chromosome, and one of skill in the art may select recombination sequences based on the gene location and toxin. In some embodiments, the recombination sequence includes a fragment or variant of lpsA1, lpsA2, dmaW1 or dmaW2.

A vector (or kit including a vector) including the nucleic acid molecules disclosed herein is also provided and includes the isolated nucleic acid sequence of a marker gene, a nucleic acid sequence of one or more telomere repeats and a recombination sequence.

A method for eliminating a target gene(s) in an endophyte is disclosed herein. The method includes the steps of integrating a nucleic acid molecule of a marker gene, a series of telomere repeats and a recombination sequence into the endophyte by homologous recombination. In some embodiments, the nucleic acid sequence is provided in a plasmid that is linearized on the telomere-distal side of the recombination sequence, and introduced into fungal protoplasts or cells. The recombination sequence targets gene(s) located in the subterminal region of a chromosome, and the recombination replaces the target gene(s). The series of telomere repeats directs spontaneous loss of the nucleic acid sequence downstream of the recombinant telomere repeats, followed by stabilization of a new chromosome end including the recombinant telomere repeats.

In some embodiments, the methods eliminate 70%, 75% or substantially all of the ergot alkaloid gene cluster. In some embodiments, a portion of the ergot alkaloid gene cluster is eliminated sufficient to affect the expression of one or more toxins in the endophyte or fungus. In some embodiments, the expression of one or more toxins in the fungus is reduced by at least 50%, 60% or 70%.

The present methods to eliminate target genes utilize homologous recombination of the exogenous DNA with the genome. In one embodiment disclosed herein, lpsA1 in *E. coenophiala* is used for the recombination sequence because it provides a long sequence that is not highly repeated in the genomes. As those skilled in the art will appreciate, homologous recombination is more likely the longer the sequence provided for homologous recombination, and the necessary recombination length, and is generally highly variable depending on the species and strain of fungus (e.g., a much smaller target may be needed for *Aspergillus nidulans* than for *Neurospora crassa*.) Thus, one of skill in the art will be able to choose the target and utilize the currently disclosed method accordingly based on the selection of the species and strain of fungus.

Endophyte and fungal strains can be produced by the methods disclosed herein, and include, in some embodiments, a recombinant nucleic acid sequence substantially lacking the ergot alkaloid gene cluster. In some embodiments, the gene dmaW or lpsB is absent from the resulting fungal strain.

In some embodiments the fungal strain is any strain of *Epichloë coenophiala*. In some embodiments, the fungal strain is any strain of *Aspergillus* species. In some embodiments, the endophyte strain is from *E. coenophiala* and the strain is selected from e19 and e4163. In some embodiments, the endophyte strain is selected from e7575, e7480 and e7479. In some embodiments, the endophyte strain includes a nucleic acid sequence of any one of SEQ ID NO: 1 or SEQ ID NO: 2.

Also disclosed herein is a synthetic combination of the endophyte strain as disclosed herein with a fescue grass or perennial ryegrass. In some embodiments, the fescue grass is a tall fescue grass.

Regarding sequences to knock out or eliminate, to completely eliminate ergot alkaloid production, in one embodiment, the target gene to eliminate is dmaW. However, one of skill can appreciate that when certain other ergot alkaloid genes are targeted, some products will be expressed and others eliminated. Because of the functional duplicates in the genome of *E. coenophiala*, while eleven genes were eliminated with a recombination sequence of lpsA1, with the exception of lpsB, the other genes had functional duplicates in the genome. Products attributable to four genes (dmaW, easF, easC, easE) were obtained, but downstream products, attributable to the additional genes—easD, easA, easG and cloA—were lacking, even though the remaining copies of all of those genes appeared functional. In a general sense, eliminating easH should eliminate ergopeptines but not ergopeptide lactams; eliminating lpsA or lpsB should eliminate ergopeptines and ergopeptide lactams; eliminating cloA should eliminate lysergic acid, ergopeptines and ergopeptide lactams; eliminating easD, easA or easG should eliminate all those plus agroclavine; eliminating easE should eliminate all those plus chanoclavine, and eliminating dmaW should eliminate all ergot alkaloids. Genes that can be targeted in the *Epichloë* and *Aspergillus* species include, genes for ergot alkaloids such as dmaW or other genes in EAS clusters, genes for tremorgenic indole-diterpenes (IDT cluster genes) [14], a cyclopiazonic acid, and genes for aflatoxins such as aflR.

Sequences of the junctions of the telomere repeats, oligotag [41], and remnant of the recombination sequence (a fragment of the lpsA gene), also described as terminal contigs in two EAS1 knockoff derivatives of *Epichloë coenophiala* e19, show the sequences expected for the chromosome end utilizing the methods described herein to provide a nontoxic endophyte (NTE) strain. The e7480-1 ΔEAS1 genome assembly included a 181-bp contig (SEQ ID NO:1) that has three telomere repeats (repeat unit TAACCC (SEQ ID NO: 35)) followed by the oligotag at positions 19-63, and partial lpsA1 sequence at positions 65-181.

Similarly, the e7479-1 ΔEAS1 assembly included a 228-bp contig (SEQ ID NO:2) with telomere sequence at positions 1-106, the oligotag at positions 107-151, and partial lpsA1 sequence at positions 153-228. Thus, both strains had assembled contigs with the sequences expected for the truncated chromosome end.

The genome sequences also demonstrated, by virtue of their absence, that other genes of the cluster were missing in those genomes. The PCR test for one such gene, dmaW2, in FIG. 3B evidences this absence. BLAST results (not shown) also shows that only one gene copy remains in each of those genomes. In addition, the only remaining copy of lpsB is that of lpsB2, and the genome sequence shows that it has the frame-shift mutation that makes it inactive (data not shown). In some instances, then, the genome sequence in the fungus after utilizing the methods of the present invention, can be defined by the absence or lack of functional copies of genes that contribute to toxicity, such as genes in an ergot alkaloid cluster.

The presently-disclosed subject matter further includes a kit that comprises a vector and instructions for using the vector according to the methods disclosed herein. In addition to the vector, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

Methods

The presently-disclosed subject matter further includes methods. A method of eliminating target gene(s) in an endophyte is provided. In some embodiments, the method includes integrating a nucleic acid molecule including a marker gene, one or more telomere repeats and a recombination sequence comprising a variant or fragment of a wild type gene of an ergot alkaloid gene cluster, a cyclopiazonic acid, an aflatoxin gene cluster, or an indole-diterpene gene cluster; or a recombination sequence with 90% identity to the nucleotide sequence of a wild type gene of said clusters with at least one substitution and/or at least one deletion modification relative to the gene(s) or a sequence with at least 50% identity to the amino acid of said gene, recombining to replace the target gene(s), wherein the nucleic acid sequence of one or more telomere repeats directs spontaneous loss of the nucleic acid sequence downstream of the recombinant telomere repeats followed by stabilization of a new chromosome end including the recombinant telomere repeats.

A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) Reeck et al. [18]. Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al. [18]). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 30%, 70%, 80% and most preferably at least about 90 or 95%) of the nucleotides match over the defined length of the DNA sequences, as determined by sequence comparison algorithms, such as BLAST, FASTA, DNA Strider, T-COFFEE, MUSCLE, MAFFT, SATE etc. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

In some embodiments, the methods produce an endophyte strain comprising a nucleic acid sequence substantially lacking all of a gene cluster. As used herein, when substantially all of the gene cluster is eliminated, at least 80%, at least 90% or at least 95% of the gene cluster sequence is absent or removed.

In some embodiments, the removal of a portion of a gene sequence sufficient to affect the function of the gene and/or gene cluster is defined as a loss in the relative expression of the gene. For example, in the removal or elimination of a portion or all of a gene and/or gene cluster, expression of the gene or some or all of the genes in the gene cluster is reduced, substantially eliminated, or eliminated (as compared to an endophyte strain in which the gene and/or gene cluster has not been reduced substantially eliminated, or eliminated). In some embodiments of the presently disclosed subject matter, for example, expression of genes in the ergot alkaloid gene cluster are reduced. In some embodiments, the relative expression of the genes can be measured before and after the removal of a portion of a gene sequence. In some embodiments, measurement of the relative expression of the genes can be measured after insertion of the genes contained in knockoff transformants of the endophyte strain. In some embodiments, a plant containing the transformed endophyte strain can be measured for relative expression of the genes. Additionally, absence of genes in the genome sequences can be verified by, for example, PCR.

Substantially homologous nucleic acid molecules specifically hybridize typically at moderate stringency or at high stringency all along the length of the nucleic acid molecule of interest. The term "binding affinity" as used herein refers to a measure of the capacity of a probe to hybridize to a target polynucleotide with specificity. Thus, the probe comprises a polynucleotide sequence that is complementary, or essentially complementary, to at least a portion of the target polynucleotide sequence. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide.

The phrase "substantially hybridizes" refers to complementary hybridization between a probe nucleic acid molecule and a substantially identical target nucleic acid molecule as defined herein. Substantial hybridization is generally permitted by reducing the stringency of the hybridization conditions using art-recognized techniques.

"Stringent hybridization conditions" and "stringent hybridization wash conditions" in the context of nucleic acid hybridization experiments are both sequence- and environment-dependent. Longer sequences hybridize specifically at higher temperatures. Generally, highly stringent hybridization and wash conditions are selected to be about 3° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. Typically, under "stringent conditions" a probe hybridizes specifically to its target sequence, but to no other sequences.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Molecular genetic techniques to precisely eliminate genes in asexual filamentous fungi require the introduction of a marker gene into the target genome. A novel strategy was developed to eliminate from fungal genomes genes or clusters of genes located in subterminal regions of chromosomes, then eliminate the marker gene and vector backbone used in the transformation procedure. Because many toxin gene clusters are subterminal, this method is particularly suited to generating non-toxigenic fungal strains. The technique was tested on *Epichloë coenophiala*, a seed-transmissible symbiotic fungus (endophyte) of the important forage grass, tall fescue. The endophyte is necessary for maximal productivity and sustainability of this grass but can produce ergot alkaloids such as ergovaline, which are toxic to livestock.

EAS1 cluster in *E. coenophiala* e19, which assembled into three contigs, GenBank accession Nos. KC989607, KC989608 and KC989609, are shown spatially relative to the telomere in FIG. 1. The contig that starts with telomere sequence is GenBank accession KC989609. Going rightward from the telomere, the first gene in that contig is lpsB, the next is easE. Then in GenBank accession KC989607 the genes continue in the order (increasingly far from the telomere): easF easG easA easH dmaW, and then in KC989608 the genes continue in the order: cloA easC easD and lpsA. The currently disclosed procedure can be used to target homologous recombination in any of the sequences to the right (centromere proximal, thus telomere-distal side) of a gene, eliminating that gene and all the genes to the left of it. In the examples provided herein, lpsA1 was targeted resulting in loss of all eleven of the EAS1 genes. Since lpsB1 is closest to the telomere, application of this approach to any region to the right of that gene would eliminate it. The result would be that ergopeptines cannot be produced. The next gene over is easE1, which is for a very early step in the biosynthetic pathway. So, eliminating it by knockoff targeting any gene to the right of it could be expected to eliminate the production of all clavine and ergot alkaloids, except that in the particular strain e19 there is a second functional gene copy for all genes except lpsB.

Genome sequence of *E. coenophiala* strain e19 revealed two paralogous ergot alkaloid biosynthesis gene clusters, designated EAS1 and EAS2. EAS1 was apparently subterminal (GenBank accession Nos. KC989607 and KC989609), and the lpsB copy in EAS2 had a frame-shift mutation (Genbank accession No. KC989611). A vector with a fungal-active hygromycin phosphotransferase gene (hph), an lpsA1 gene fragment for homologous recombination at the telomere-distal end of EAS1, and a telomere-repeat array positioned to drive spontaneous loss of hph and other vector sequences, and to stabilize the new chromosome end was designed. Strain e19 of *E. coenophiala* was transformed with this vector and knockoff endophyte strains were selected, which were confirmed by genome sequencing to lack 162 kb of a chromosome end including most of EAS1, and also to lack vector sequences. These ΔEAS1 knockoff strains produced no detectable ergovaline, whereas complementation with functional lpsB restored ergovaline production.

Example 1

Identification of EAS gene clusters in *E. coenophiala*. The genome assembly for *E. coenophiala* e19 included two copies each of the eleven EAS genes known to be required for ergovaline production (FIG. 1), although the assembly did not contain the EAS clusters entirely within individual scaffolds. As is typical of EAS clusters in *Epichloë* spp. (20), regions flanking and between EAS genes were primarily composed of very AT-rich repeats, which probably interfered with complete assemblies of the clusters. However, the previously reported genome sequence of another *E. coenophiala* strain, e4163, had one scaffold with its entire EAS1 cluster (GenBank KC989569.1) and another with its entire EAS2 cluster (GenBank KC989570.1) [19]. The cluster with genes most similar to those of *E. festucae* was designated EAS2, the other was designated EAS1, and the orthologous copies in e19 were identified by identity or near identity of their nucleotide sequences to those of the corresponding cluster in e4163. Assuming that the gene arrangements in e19 are similar to those in e4163, tentative maps were generated and are given in FIG. 1. The only EAS genes in e19 that lacked orthologues in e4163 were lpsB1 and easE1, which assembled together on an 18,217 bp single-contig scaffold of the e19 assembly (GenBank accession KC989609.1). That scaffold terminated in a canonical telomere repeat array (SEQ ID NO: 55 CCCTAACCCTAACCCTAACCCTAACCCTAACCCTAT) downstream of lpsB1, indicating that if e19 had a single complete EAS1 cluster it was located at a chromosome end.

Example 2

Identification of putative MAST chromosome-end knockoff strains. Transformation plasmid pKAES329 was constructed with a large segment of lpsA1 sequence to target homologous integration, an hph selectable marker modified for expression in fungi to confer resistance to hygromycin B, and a telomere repeat array adjacent to the lpsA1 sequence to eventually separate hph and the rest of the vector backbone from the lpsA1 sequence.

The lpsA1 gene fragment of SEQ ID NO:3 was used in chromosome-end knockoff vector pKAES329.

In a screen of 192 hygromycin B-resistant transformants of *E. coenophiala* e19, three were identified that tested negative for dmaW1 and positive for dmaW2, as expected if the linearized pKAES329 had integrated by homologous recombination at lpsA1, causing loss of the corresponding chromosome end. These three transformants were designated, with genotypes, as e7479 ΔEAS1, e7480 ΔEAS1 and e7481 ΔEAS1 (abbreviated as e7470, etc.). A similar screen of 67 transformants of *E. coenophiala* e7135 ΔdmaW2 [13] revealed one putative chromosome-end knockoff strain designated e7575 ΔdmaW2 ΔEAS1 (abbreviated as e7575).

Example 3

Figure 2:
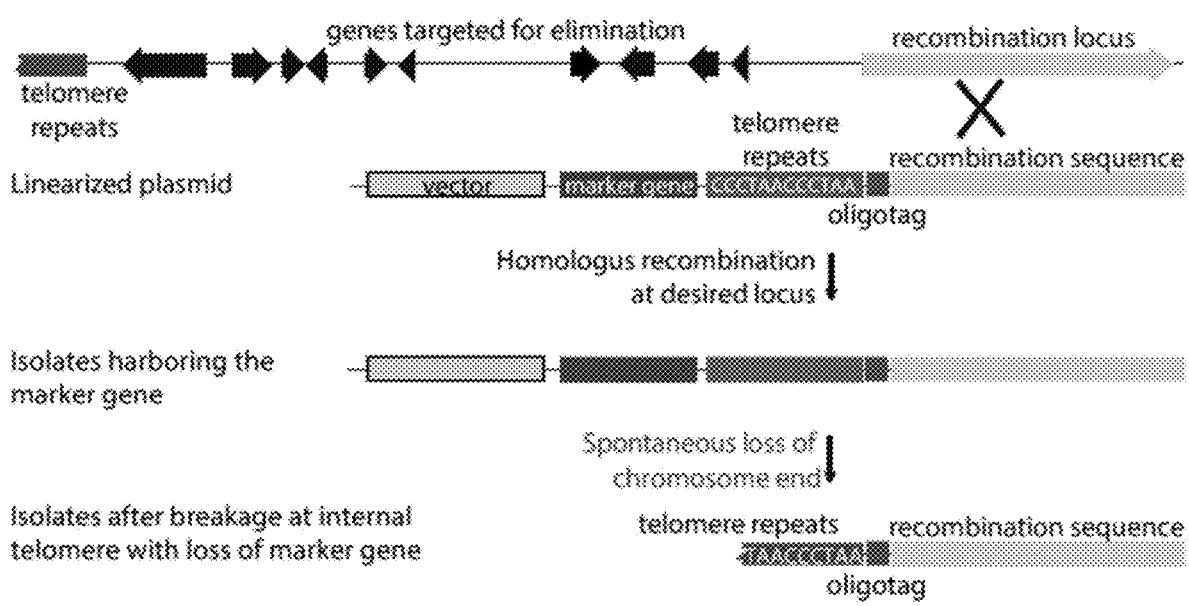
FIG. 2 includes a schematic representation of the chromosome-end "knockoff" [41] strategy for elimination of toxin genes. The plasmid is linearized on the telomere-distal side of the recombination sequence, and introduced into fungal protoplasts. Transformants are selected based on the selectable marker, such as the hph gene for hygromycin B resistance. If the plasmid has integrated by homologous recombination, genes between the recombination sequence and the chromosome end should be lost in the absence of selection because they are no longer linked to a centromere-containing chromosome. Subsequent breakage at the introduced telomere repeat array results in loss of the selectable marker and vector backbone, and the remaining telomere stabilizes the new chromosome end.
Figure 3:
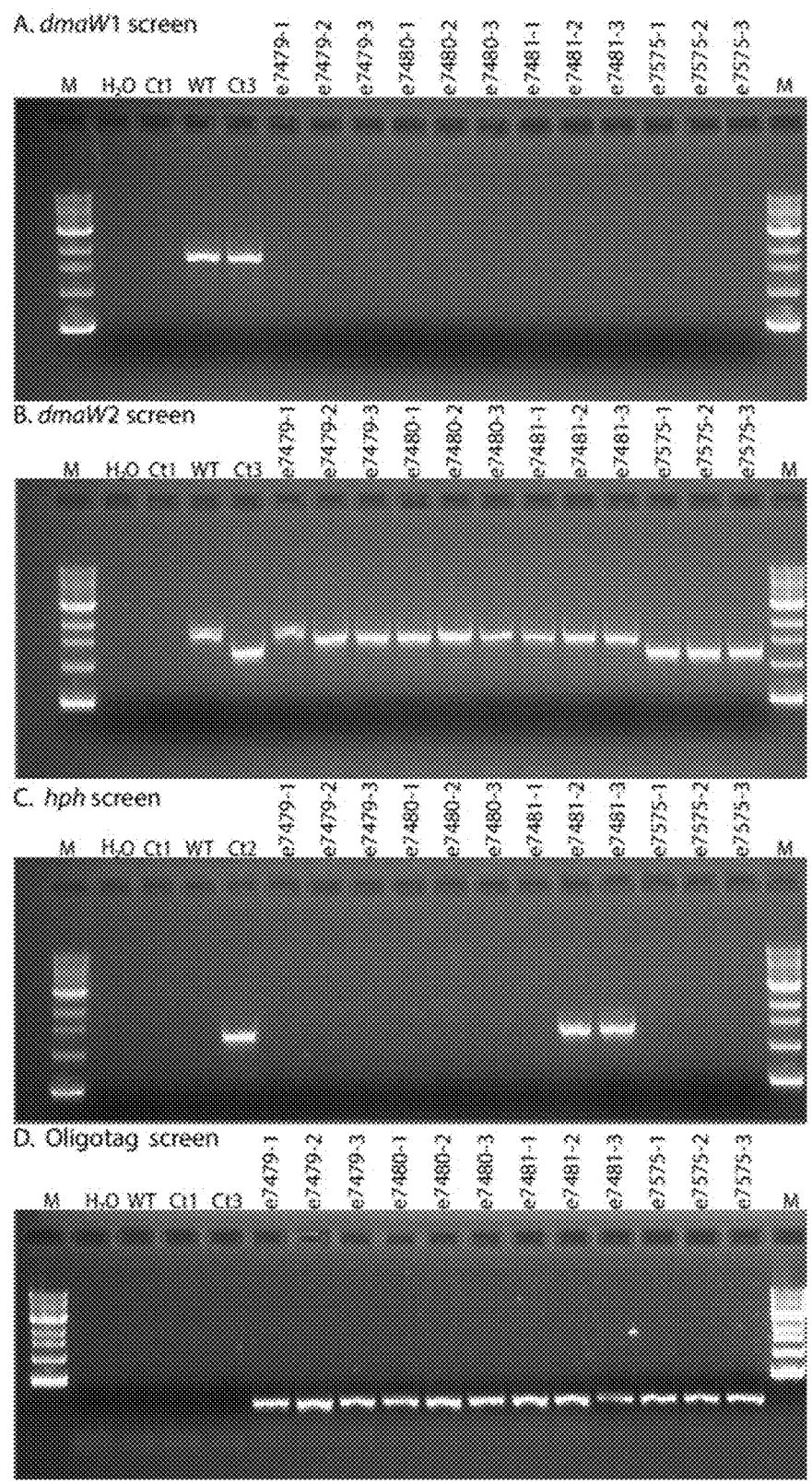
FIG. 3 provides A. Results of PCR test of single-spore isolates of putative ΔEAS1-knockoff transformants with primers specific for dmaW1 from the EAS1 cluster; B. Results of PCR with primers specific for dmaW2 from the EAS2 cluster; C. Results of PCR tests for hph; and D. Results of PCR tests for the introduced sequence ("oligotag") [41] linked to the lpsA1 remnant. Controls (see [13]) are: $H_2O$=no template PCR control; WT=e19, with both dmaW1 and dmaW2; Ct1=*Epichloë uncinata* e167, which lacks all EAS genes; Ct2=*E. coenophiala* e7133, a derivative of e19 that possesses dmaW1 but has an hph cassette in place of a partial deletion in dmaW2; Ct3=e7135, which is derived from e7133 by Cre-mediated elimination of the hph cassette.

Tests for spontaneous losses of vector sequences. For each of the putative knockoff strains, three single spores were randomly chosen and tested by the same PCR screen, confirming the apparent loss of dmaW1 and retention of dmaW2 (FIG. 3A, 4B). Without being bound by theory, spontaneous breakage at the internal telomere repeat was expected to lead to loss of hph and the vector backbone with all foreign DNA except the oligotag (FIG. 2). To check for such events, unselected single-spore isolates were screened by PCR for hph (FIG. 3C). For two of the transformants (e7479 ΔEAS1 and e7480 ΔEAS1) all single-spore isolates tested negative for hph, whereas for the third transformant (e7481 ΔEAS1) two out of three single-spore isolates tested positive for hph. All three unselected single-spore isolates from e7575 ΔdmaW2 ΔEAS1 tested negative for hph. These strains were also confirmed to contain the oligotag, based on PCR with one primer sequence contained within the oligotag and the other primer sequence contained within the lpsA1 remnant (FIG. 3D).

Figure 4:
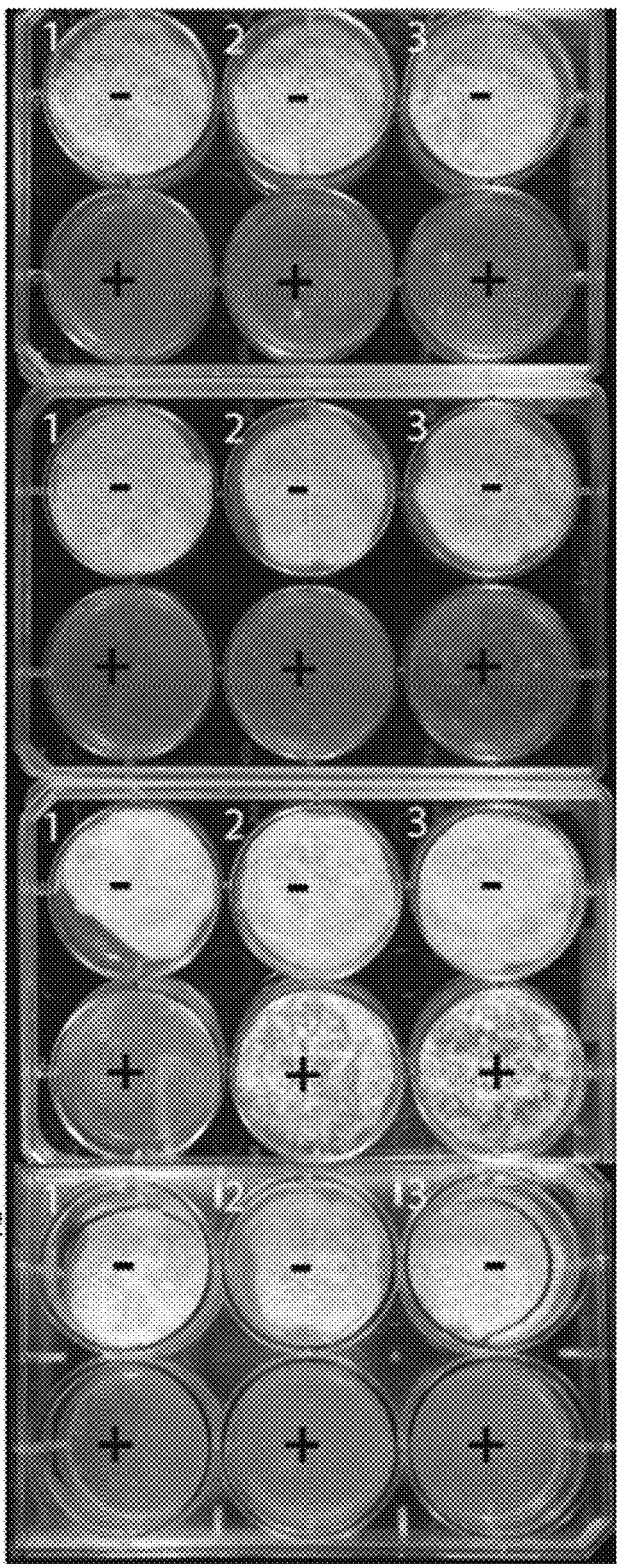
FIG. 4 shows results of tests for sensitivity to hygromycin B. All single-spore isolates of e7479 ΔEAS1, e7480 ΔEAS1 and e7575 ΔdmaW2 ΔEAS1 failed to grow on selective medium (+), whereas two of the single-spore isolates of e7481 ΔEAS1 retained the ability to grow on selective medium.

To confirm loss of hph, the single-spore isolates were tested for sensitivity to hygromycin B. All isolates that tested negative for hph by PCR were sensitive to the antibiotic, whereas the two hph-positive single-spore isolates from e7481 ΔEAS1 retained the ability to survive on selective medium. Similarly, all spores derived from e7575 ΔdmaW2 ΔEAS1 failed to grow on medium with hygromycin B (FIG. 4). The two transformants that showed no retention of hph or hygromycin B resistance were considered to be confirmed ΔEAS1 knockoff derivatives of e19, and for each a single spore isolate (e7479-1 ΔEAS1 and e7480-1 ΔEAS1) was maintained for further study.

Example 4

Genome sequencing of knockoff strains. Inspection of assembled genome sequences of e7479-1 ΔEAS1 and e7480-1 6EAS1 by BLASTn revealed the EAS2-cluster genes, but none of the EAS1-cluster genes, as expected for EAS1 chromosome-end knockoffs. The BLAST queries for the genomes are provided as Appendix A. Furthermore, there were no other sequences from the transformation vector except the expected lpsA1 remnant and the 45-bp noncoding oligotag sequence.

Inspection of e7479-1 and e7480-1 genome sequence assemblies confirmed the presence and location of the oligotag as expected. The e7480-1 genome assembly included a 181-bp contig of SEQ ID NO:1. This has telomere repeats at positions 1-21, the oligotag at positions 19-63 (the first three bp overlapping with the telomere sequence), and lpsA1 sequence at positions 65-181. Similarly, the e7479-1 assembly included a 228-bp contig with telomere sequence at positions 1-109, the oligotag at positions 107-151, and partial lpsA1 sequence at positions 153-228.

Alkaloid profiles in symbio. Ergovaline and ergine were undetected in the plants with serial numbers 6105 and 6106, which were symbiotic with the ΔEAS1 knockoff strains. However, ergotryptamine, an early pathway spur product [20] and chanoclavine I were at higher concentrations than in the plants with the wild-type strain (Table 1). Plants with the lpsB-complemented strain, e7605 ΔEAS1 lpsB, accumulated chanoclavine I, ergine and ergovaline to concentrations similar to those of plants with the wild-type strain, but chanoclavine I and ergotryptamine were also observed in those plants. No ergot alkaloids were detected in plants symbiotic with e7575-1 ΔdmaW2 ΔEAS1.

Plants symbiotic with the knockoff strains had profiles of loline alkaloid similar to those with the wild-type strain e19 (data not shown).

TABLE 1

Ergot-alkaloid profiles in tall fescue pseudostems with endophyte strains.[a]

| Endophyte strain | Endophyte genotype | Ergovaline (nmol/g) | Ergine (nmol/g) | Ergotryptamine (nmol/g) | Chanoclavine I (nmol/g) |
|---|---|---|---|---|---|
| e19 | WT | 12.6 ± 4.1 | 2.7 ± 1.6 | 2.7 ± 2.1 | 3.0 ± 2.2 |
| e7479-1 | ΔEAS1 | 0.0 | 0.0 | 86.7 ± 74 | 5.6 ± 3.7 |
| e7480-1 | ΔEAS1 | 0.0 | 0.0 | 100.0 ± 41 | 5.3 ± 1.2 |
| e7605 | ΔEAS1 lpsB | 12.1 ± 6.8 | 2.1 ± 1.3 | 112.7 ± 75 | 2.5 ± 1.3 |

[a]Alkaloid concentrations are estimated averages ± standard error of the mean for five replicates.

Symbiotic stability of the knockoff strains. After seedling inoculation with the endophyte strains the tall fescue plants were grown in the greenhouse for ca. one year, then planted in the field where they vernalized over winter and then set seeds. In seed tests, strong PCR-positive results indicated that at least 96% had E. coenophiala, and the other 4% were considered nondefinitive because they gave less PCR product. Thus, endophyte seed transmission for the first seed harvest was high (≥96% infection rate) for both e7479-1 ΔEAS1 and e7480-1 ΔEAS1 knockoff strains. The ergot alkaloid profile of samples derived from these seeds, was similar to the profile of vegetative tissues derived from plants associated with the knockoff strains, except that they had proportionally much less ergotryptamine (Table 2).

TABLE 2

Ergot alkaloid profile and estimated concentrations of first generation seeds.

| Plant series[a] | Endophyte genotype | Ergovaline nmol/g | Ergine nmol/g | Ergotryptamine nmol/g | Chanoclavine nmol/g |
|---|---|---|---|---|---|
| 6105 | e7479-1 ΔEAS1 | 0.0 | 0.0 | 9.0 | 0.8 |
| 6105 | e7479-1 ΔEAS1 | 0.0 | 0.0 | 8.7 | 0.8 |
| 6106 | e7480-1 ΔEAS1 | 0.0 | 0.0 | 9.3 | 0.8 |
| 6106 | e7480-1 ΔEAS1 | 0.0 | 0.0 | 6.4 | 0.7 |
| 6107 | e19 WT | 9.4 | 7.9 | 1.1 | 1.4 |
| 6107 | e19 WT | 10.3 | 7.9 | 1.5 | 1.8 |

[a]Each sample was a pool of seeds from five plants of the same series.

Discussion

Many years of research have established that CTE E. coenophiala provides numerous fitness enhancements to tall fescue cultivars used throughout much of the U.S. [3, 4, 9]. Most such cultivars and the naturalized populations of tall fescue in North America, Australia and New Zealand have northern European origins, and the strict vertical transmission and ubiquity of CTE strains in tall fescue throughout northern Europe [21-23]) suggest that the hosts and endophytes are closely co-adapted. It was rationalized, therefore, that surgically eliminating toxin-production genes from a CTE strain would probably generate nontoxic strains that retain the vast majority and magnitude of benefits to the plant. However, currently available techniques for such genetic manipulations in asexual fungi necessarily leave transgenes. (In contrast, for sexual species crossing strategies can eliminate such transgenes.) In a previous study [13] we employed marker-exchange mutagenesis with a loxP-flanked hph selection marker, screened for the desired gene replacement, and then transiently transformed the mutant with a Cre recombinase gene to eliminate hph. Though effective, this approach was far more intensive and expensive than the alternative presented here, whereby we targeted telomere-associated clusters of genes. By sequencing genomes of E. coenophiala e4163 and e19 [8], it was determined that the EAS1 cluster was subterminal, and also that lpsB2 a key ergovaline-synthesis gene in the e19 EAS2 cluster, was probably inactive. A strategy was then devised to generate chromosome-end knockoff mutants lacking the EAS1 cluster. To do so required a vector that contained a telomere-repeat array to stabilize the resulting chromosome end, but that sequence was positioned such that the vector, including hph, would be lost upon breakage at the introduced telomere. The main risk was that hph might be insufficiently stable in the transformants for initial selection. In fact, hygromycin B-resistant transformants were recovered, and those with the target-site integration were identified based on marker instability after single-spore isolation on nonselective medium. Using this strategy, ca. 162 kb of the EAS1 gene cluster from the genome of strain e19 was eliminated, and similarly EAS1 was knocked off from strain e7135, a ΔdmaW2-knockout produced previously [13]. As expected, the e19 ΔEAS1 strains produced no ergovaline, and the ΔdmaW ΔEAS1 strain produced no ergot alkaloids.

Since sequences of the EAS2-cluster genes suggested that all could be functional except lpsB2, we expected that plants with the ΔEAS1 knockoff strains would accumulate lysergic acid as previously shown for an lpsA knockout strain of a perennial ryegrass endophyte [24, 25]. However, the ΔEAS1 strains produced no detectable lysergic acid or even the intermediate tetracyclic clavines. Instead, the ergot-alkaloid profiles were dominated by ergotryptamine and chanoclavine I, similar to the profile previously observed when the four early-pathway genes (dmaW, easF, easC and easE) from Neosartorya fumigata were introduced into the ergot-alkaloid nonproducer, Emericella nidulans [26]. Ergotryptamine is a spur-product produced in Em. nidulans expressing dmaW, easF and easC, as well as several unmodified Epichloë species including E. coenophiala [20], whereas chanoclavine I is an intermediate in the pathway to lysergic acid. Since ergovaline production was restored by complementation with a functional lpsB, the other genes in the EAS2 clusters are apparently functional. However, the relatively high level of ergotryptamine in the ΔEAS1 strains as well as the lpsB-complemented strain suggests that the EasE2 protein may not be fully active. Sequence comparisons of e19 easE2 with easE in other Epichloë species known to produce ergot alkaloids indicated a nonsynonymous mutation at codon 230, giving a serine in place of the otherwise conserved proline. Even if this P230S mutation affected EasE2 function, the production of chanoclavine I by the ΔEAS1 strains indicated that EasE2 had at least some activity (unless another unknown enzyme provided complementary activity). Furthermore, the alkaloid profile of the complemented strain, with levels of ergovaline and ergine similar to wild-type e19, suggested more complex dynamics than just a bottleneck at the EasE step.

Developing and deploying the currently disclosed technology to generate non-transgenic, yet genetically altered strains, avoids risk either real or perceived associated with transgenic organisms. Existing methods for surgical genetic manipulation of asexual fungi require introduction of marker genes derived from other organisms. Such exogenous ("foreign") genes pose public and regulatory concerns, especially since these endophytes are to be deployed in cultivars that are meant to persist in pastures for decades. Once planted, it may be difficult or impossible to eradicate the plant with its modified endophyte should concerns arise about a transgene in the endophyte genome. Therefore, it is important to address up front the regulatory and public concerns associated with genetically modified organisms. The nature of the presently disclosed knockoff strains was reviewed by the Animal and Plant Health Inspection Service (APHIS) and determined not to fall under their regulation. It is noted that the alkaloid profiles of plants with the knockoff strains are similar to those of some naturally occurring grass-*Epichloë* species symbiota that accumulate chanoclavine as an end product [19]. In rats, chanoclavine I exhibits no appreciable effect on dopamine receptors [27] and prolactin levels [28]. Ergotryptamine is a recently identified ergot alkaloid [20] for which the biological activities are yet to be determined.

Small animal and livestock feeding studies would determine the effects, if any, of the simple ergot alkaloids associated with the ΔEAS1 knockoff strains. Future plant performance studies in the field, during which the specific alterations in the genome, including the 45-bp oligotag, will facilitate monitoring strain persistence in plant lines and field plots, and possible movement in agroecosystems.

Materials and Methods

Biological materials. The wild type *Epichloë coenophiala* strain e19 (=ATCC 90664), was isolated from tall fescue (*Lolium arundinaceum*=*Schedonorus arundinaceus*=*Schedonorus phoenix*=*Festuca arundinacea*) cv. Kentucky 31 (28), and *Epichloë coenophiala* strain e4163 was isolated from a tetraploid *Lolium arundinaceum* plant (PI #422777 from Western Regional Plant Production Station, Pullman, Wash.). The *E. coenophiala* strain e7135 [13], was derived from e19 by replacing the ergot alkaloid biosynthesis gene dmaW2 with a hygromycin B-resistance gene (hph), followed by elimination of hph. These and other strains generated in this study were cultured and maintained as described in Florea et al. [30]. The *E. coenophiala* strains generated in this study, and their respective genotypes, were designated e7479 ΔEAS1, e7480 ΔEAS1 and e7481 ΔEAS1 derived from e19, e7575 ΔdmaW2 ΔEAS1 derived from e7135 ΔdmaW2, and the lpsB-complemented strain e7605 ΔEAS1 lpsB generated from e7479 ΔEAS1. Single-spore isolates of each strain are designated e7479-1, e7479-2, and so forth.

Because *E. coenophiala* is not contagious, and cannot move into a plant except by vertical transmission in seeds, new plant lineages symbiotic with endophyte strains are established by artificial inoculations [31]. Endophyte-free seeds of tall fescue elite breeding line KYFA0601 were germinated and the seedlings inoculated with *E. coenophiala* strains by the method of Chung et al. [32]. Each strain was introduced into 100 seedlings, of which ca. 80% survived after inoculation. The inoculated seedlings were planted in soil and allowed to grow in the greenhouse to produce multiple tillers. The bases of two vegetative tillers from each plant were assayed for endophyte presence by tissue-print immunoblot with antiserum raised against *E. coenophiala* protein (33). The resulting plants that were symbiotic with each strain were numbered as follow: number 6105 had e7479 ΔEAS1, number 6106 had e7480 ΔEAS1, number 6107 had wild-type e19, number 6212 had e7575 ΔdmaW2 ΔEAS1, and number 6221 had e7605 ΔEAS1 lpsB.

Molecular methods. Fungal DNA was isolated from fresh mycelium using ZR Fungal/Bacterial DNA MiniPrep kit (Zymo Research, Irvine, Calif., USA), or using Geno/Grinder 2000 (SPEX CertiPrep, Metuchen, N.J., USA) and DNeasy 96 Plant Kit (Qiagen, Valencia, Calif., USA). Plasmid DNA was isolated from bacterial cultures using the ZR Plasmid Miniprep-Classic kit (Zymo Research, Irvine, Calif., USA). The mRNA was isolated from plant material using RNeasy Plant Mini Kit (Qiagen). PCR screens were performed using AmpliTaq Gold, and AmpliTaq Gold PCR buffer provided by the manufacturer (Applied Biosystems, Foster City, Calif., USA). For vector construction, the PCR amplifications were performed with Phusion Hot Start High-Fidelity DNA Polymerase (Thermo Scientific, Ratastie, Vantaa, Finland) with HF buffer (with 1.5 mM MgCl2) provided by the manufacturer. The temperature conditions were 98° C. for 3 min, followed by 35 cycles of 98° C. for 10 s, 62° C. for 10 s, and 72° C. for 7 min, then a final 5 min incubation at 72° C. The oligonucleotides used in this study were from Integrated DNA Technologies (Coralville, Iowa, USA), and are listed in Table 3.

TABLE 3

Primers Used in the Study

| Primer name | Sequence | SEQ ID NO: |
|---|---|---|
| lpsA1SpeI(f) | GGGACTAGTTAAGAAGCGCTTACGCCGTTCC | 5 |
| lpsA1MluI(r) | CACACGCGTAGCTGTCGTATGAAGGCACGAT | 6 |
| polylinkerDdeI | /5'Phos/TAAGCTCGAGGCCATGATGGCCTTTAAAGTCTACGTACTCA | 7 |
| polylinkerSpeI | /5'Phos/CTAGTGAGTACGTAGACTTTAAAGGCCATCATGGCCTCGAGC | 8 |
| dmaWe19copy2(+)-1d | AGAAACAGACAGGGCTATTC | 9 |
| dmaWe19copy2-(-)-5u | CTCGCCGGCATGCGTCAAAA | 10 |
| dmaw1(f) | TTATTGGATGAAACCTTAGCTAGTTGG | 11 |
| dmaWe19(-)-10 | CTCGCCGGCATGCGTCAAAT | 12 |
| 144lpsBDraI(f2) | CACTTTAAACCTAATGCACTACACTAAGACCCC | 13 |
| 144lpsB(r) | AATCTGGCCAACATGGTTCCCATG | 14 |
| 215hphlpsB(f) | GCTTGACAAACGCACCAAGTTATCG | 15 |
| 215lpsBhph(r) | TGTACACCACTTCAACGAGGCTTG | 16 |
| hph.3d | CGAAGTTATCTCGACGGTATCG | 17 |
| hph.3u | TCGGCGAGTACTTCTACACA | 18 |
| RTq-E.c.easE(f) | TCCTTGCCACCAAGGCAGATTG | 19 |
| RTq-E.c.easE(r) | ACATTGTCCACGGCAAGCCCTC | 20 |
| RTq-E.c.easA(f) | CGTGCGGATAATGAAGGCGTCC | 21 |
| RTq-E.c.easA(r) | CGATGAGAAATCCATTGGCACCG | 22 |
| RTq-E.c.easC(f) | GGCATGGCAGTCAAGTTCTTCAC | 23 |
| RTq-E.c.easC(r) | ACATTGGCTGTCCAAGTAGGGT | 24 |
| RTq-E.c.easF(f) | CCCAGAACTTTCGTCATGTCCG | 25 |
| RTq-E.c.easF(r) | ATCCCGTCCAGTGGCGGAAGTA | 26 |
| RTq-E.c.easG(f) | TTGCCAAGACTCTCCATGAGAT | 27 |
| RTq-E.c.easG(r) | ACCACGTCGGTCTTAATACAGCG | 28 |

TABLE 3-continued

Primers Used in the Study

| Primer name | Sequence | SEQ ID NO: |
|---|---|---|
| oligoscreen(f) | GATGGCCTTTAAAGTCTACGTACTC | 29 |
| lpsAoligo(r) | ATATCATGGCAACATTCAGCGCAC | 30 |

Genome analysis. Genome sequencing and assembly were performed at the Advanced Genetic Technologies Center of the University of Kentucky, and all genome assemblies were done with Newbler 2.8 (Roche Diagnostics/454 Life Sciences Corporation). The genome of the wild-type E. coenophiala strain e19 was sequenced by a combination of pyrosequencing (Roche) of sheared DNA fragments and Sanger sequencing of fosmid-cloned ends [14]. Pyrosequencing reads totaled 6,008,281, giving 2,219,715,337 nucleotide calls. These included 84,573 ditags, of which 49,817 were in the same scaffold (average distance=2.7 kb±0.8 kb). The 19,471 sequenced fosmid ends (totaling 14,229,733 bp) gave 7143 read-pairs, of which 3104 assembled in the same scaffold at 36,371±9093 bp distance (range=18,185-54,556 bp). In total, 2,201,579,615 nt assembled into 95,835,721 bp in 15,240 contigs, and the total inferred lengths of the 5640 scaffolds was 99.6 Mb (including unsequenced gaps), with N50=39,442 bp in 567 scaffolds (approx. 22-fold coverage).

The genome of e7479 ΔEAS1 was sequenced by a combination of Ion Torrent PGM (Life Technologies) and 454 pyrosequencing (Roche Diagnostics) to give 2,790,692 Ion Torrent reads totaling 454,053,270 nt, and 855,760 extended pyrosequencing reads totaling 628,200,560 nt. Assuming a 99.6 Mb genome size (from the scaffold assembly of e19), this was 10.9-fold coverage. Assembly with Newbler 2.8 gave 46,534 contigs totaling 87,313,881 bp, of which 32,285 large contigs 500 bp) totaled 83,439,153 with N50=3871 bp.

The genome of e7480 ΔEAS1 was sequenced on the MiSeq platform (Illumina, San Diego, Calif., USA) to give 22,358,620 reads at 250 cycles, totaling 4,711,677,366 high-quality bases. This was an estimated 47-fold coverage. Assembly with CLC Genome Workbench 8.0 (CLC Bio LLC, Waltham, Mass., USA), with default parameters, gave 41,794 contigs totaling 70,103,076 bp, N50=9061 bp. Approximately equal base representations of A, T, G and C in the total assembly indicated that the AT-rich intergenic regions were underrepresented in this assembly.

Plasmid constructs. A previously cloned telomere repeat array from Epichloe jestucae consisting of 26 tandem repeats of CCCTAA (SEQ ID NO: 31), was excised with Sau3AI and DdeI. In addition, a 45-bp synthetic "oligotag" (5'-TAAGCTCGAGGCCATGATGGCCTTTAAAGTC-TACGTACTCACTAG-3') (SEQ ID NO: 4) was derived from two complementary oligonucleotides (polylinkerDdeI and polylinkerSpeI) that were annealed to provide restriction endonuclease cleavage sites DdeI, DraI, RsaI, SnaBI, and SpeI. The oligotag was cleaved with DdeI and SpeI, and ligated to the 3' side of the telomere repeat array and the correspondingly digested vector pKAES215 (34) to give plasmid pKAES327 (FIG. 5A). Then a hygromycin B-resistance gene cassette Pro$_{tubB}$-hph (designated hph herein) [35] was ligated into the BamHI site of pKAES327 at the 5' side of the telomere repeat array to give pKAES328 (FIG. 5B). This plasmid can be further modified by introducing a recombination sequence from near a chromosome end into the oligotag, such that homologous recombination will generate a "knockoff" of the genes between the target sequence and the telomere. In this study, plasmid pKAES329 (FIG. 5C) was designed to knock off EAS1 in E. coenophiala, and was generated by PCR-amplifying with primers lpsA1SpeI (f) and lpsA1MluI(r) a 6944bp fragment of the E. coenophiala e19 lpsA1 gene, digesting the PCR product with SpeI and MluI, and ligating it into the SpeI and MluI sites in the oligotag of correspondingly digested pKAES328.

To construct the lpsB-complementation plasmid pKAES362, pKAES215 was digested with SpeI, end-repaired using End-it DNA End Repair kit (Epicentre, Madison, Wis., USA) and then digested with XbaI. The digested vector was ligated, using the Fast-Link DNA ligation kit (Epicentre), to a fragment containing the lpsB gene and its native promoter (from Epichloë festucae×typhina strain LpI), which had been generated by PCR with primers 144lpsBDraI(f2) and 144lpsB(r) and then digested with XbaI and DraI.

Fungal transformation. Epichloë coenophiala isolates were grown in potato dextrose broth and the protoplasts were prepared and transformed using the polyethylene glycol (PEG) method as described previously [13, 24], except that, prior to transformation, the plasmid DNA was incubated for 30 min with 10 µg of Lipofectin Transfection Reagent (Life Technologies). Protoplasts of E. coenophiala e19 and e7135 were transformed with 6-10 µg of pKAES329 DNA linearized with MluI. The complementation transformation was performed with 8 µg of pKAES362 linearized with XbaI. The protoplasts were then suspended in 7 ml CRM-low (complete regeneration medium containing low melting agarose from Seakem LE, FMC Bioproduct, Rockland, Me.) [24], and poured over 20 ml CRM plates containing hygromycin B (Calbiochem, San Diego, Calif.) to give a final concentration of 50 µg/ml. The transformation plates were incubated at 21° C. for 4-5 weeks. For the chromosome-end knockoff experiment the fungal transformants were transferred onto potato dextrose agar (PDA) without hygromycin B (nonselective medium) for sporulation, and then single-spore isolated on nonselective medium. For the complementation experiment the transformants were maintained on PDA containing hygromycin B.

Screening of the knockoff and complementation transformants. To identify putative ΔEAS1 knockoffs the fungal transformants were screened by PCR as follows. DNA was extracted with the DNeasy 96 Plant Kit (Qiagen, Valencia, Calif., USA) and screened by PCR with primers specific for dmaW1 [dmaW1(f) and dmaWe19(−)-10] and dmaW2 (dmaWe19copy2.1d and dmaWe19copy2.5u). All of the putative knockoffs were also screened for the presence or absence of hph by PCR with the primer pair hph.3d and hph.3u. For complementation of the ΔEAS1 knockoff strain the transformants were screened for integration of the lpsB-containing plasmid by PCR with the primer pair 215hphlpsB (f) and 215lpsBhph(r). The PCR reactions were carried out in 25 µl reaction mixtures with 5-10 ng DNA template, 200 µM each dNTP, 0.2 µM each primer, 2.5 units AmpliTaq Gold, and AmpliTaq Gold PCR buffer with MgCl$_2$ (1.5 mM final conc.) provided by the manufacturer (Applied Biosystems, Foster City, Calif., USA), in a model 2720 Thermal Cycler (Applied Biosystems). The temperature regime was as follows: 9 min at 95° C., 35 cycles of 94° C. for 30 s, annealing temperature (61° C. for dmaW2, 57° C. for lpsB-hph, 59° C. for dmaW1 and hph) for 35 s, 72° C. for 2 min, and then a final 7 min incubation at 72° C.

Antibiotic sensitivity tests. Mycelium of each putative ΔEAS1 knockoff strain was ground in 500 μl sterile water and aliquots were spread on PDA with and without hygromycin B (50 μg/ml) in wells of Falcon 6-well plates (Becton Dickinson and Co., Franklin Lakes, N.J.). The plates were incubated 4 wk at 21° C.

Ergot and loline alkaloid analyses. Alkaloid profiles were determined from one-year-old plants symbiotic with the *E. coenophiala* strains, and five independently inoculated plants were analyzed for each strain. Ergot alkaloids were extracted from 20-50 mg of freeze-dried tall fescue pseudostems and analyzed by high-pressure liquid chromatography (HPLC) as previously described [36] based on the method of Spiering et al. [37]. Loline alkaloids were extracted from 50 mg of freeze-dried pseudostems and analyzed by GC-MS as described by Blankenship et al. [38].

Seed transmission tests. The plants of elite breeding line KYFA0601 symbiotic with *E. coenophiala* e7479-1 ΔEAS1 and 7480-1 ΔEAS1 were grown in the greenhouse for one year, then planted and vernalized in the field. The seeds were harvested from each plant and stored separately at 20° C. For each of the two knockoff strains, ten plants were checked for endophyte transmission by analysis of eight seeds each as follows. DNA was extracted using the DNeasy 96 Plant Kit (Qiagen, Valencia, Calif., USA) according to the manufacturer's instructions, except that plates with arrayed seeds were immersed in liquid nitrogen for 30 s immediately prior to maceration with the Geno/Grinder 2000. The PCR screen for the presence of the oligotag (SEQ ID NO:4) linked to remnant lpsA1 was performed with primers oligoscreen(f) and lpsAoligo(r) and the following program: 9 min at 95° C., 35 cycles of 94° C. for 30 s, 59° C. for 35 s, 72° C. for 1 min, and then a final 7 min incubation at 72° C.

Throughout this document, various references are mentioned. All such references are incorporated herein by reference, including the references set forth in the following list:

DEPOSIT INFORMATION

*Epichloe coenophiala* strains e7479 and e7480 were deposited with the American Type Culture Collection (ATCC), 10801 University Boulevard, Manassas, Va. 20110 USA, on Feb. 25, 2020 and given Accession Numbers PTA-126678 and PTA-126679, respectively. *Epichloë coenophiala* strains e7479 and e7480 contain a deletion in EAS1 and comprise SEQ ID NO:2 and SEQ ID NO: 1, respectively. Applicant has or intends to comply with all the requirements set forth in 37 C.F.R. §§ 1.801-1.809.

REFERENCES

1. Joost R E: Conservation: erosion control, soil management and remediation, and effects on wildlife habitat. In: *Tall Fescue for the Twenty-first Century*. Edited by Fribourg H A, Hannaway D B, West C P. Madison, Wis.: American Society of Agronomy, Crop Science Society of America, Soil Science Society of America; 2009: 489-507.
2. Siegel M R, Johnson M C, Varney D R, Nesmith W C, Buckner R C, Bush L P, Burrus P B, II., Jones T A, Boling J A: A fungal endophyte in tall fescue: incidence and dissemination. *Phytopathology* 1984, 74:932-937.
3. Malinowski D P, Belesky D P: Ecological importance of *Neotyphodium* spp. grass endophytes in agroecosystems. *Grassland Science* 2006, 52:1-14.
4. Schardl C L, Florea S, Pan J, Nagabhyru P, Bec S, Calie P J: The epichloae: alkaloid diversity and roles in symbiosis with grasses. *Curr Opin Plant Biol* 2013, 16:480-488.
5. Nagabhyru P, Dinkins R D, Wood C L, Bacon C W, Schardl C L: Tall fescue endophyte effects on tolerance to water-deficit stress. *BMC Plant Biology* 2013, 13:127. doi: 110.1186/1471-2229-1113-1127.
6. Timper P, Gates R N, Bouton J H: Response of *Pratylenchus* spp. in tall fescue infected with different strains of the fungal endophyte *Neotyphodium coenophialum*. *Nematology* 2005, 7:105-110.
7. Florea S, Panaccione D G, Schardl C L: Ergot alkaloids of the family Clavicipitaceae. *Phytopathology* 2017, 107: 504-518.
8. Florea S, Phillips T D, Panaccione D G, Farman M L, Schardl C L: Chromosome-end knockoff strategy to reshape alkaloid profiles of a fungal endophyte. *G3: Genes—Genomes—Genetics* 2016, 6:2601-2610.
9. Hopkins A A, Young C A, Simpson W R, Panaccione D G, Mittal S, Bouton J H: Agronomic performance and lamb safety of tall fescue novel endophyte combinations in the south central USA. *Crop Sci* 2010, 50:1552-1561.
10. Hopkins A A, Young C A, Butler T J, Bouton J H: Registration of Texoma MaxQ II tall fescue. *Journal of Plant Registration* 2011, 5:14-18.
11. Watson R H, McCann M A, Parish J A, Hoveland C S, Thompson F N, Bouton J H: Productivity of cow-calf pairs grazing tall fescue pastures infected with either the wild-type endophyte or a nonergot alkaloid-producing endophyte strain, AR542. *J Animal Sci* 2004, 82:3388-3393.
12. Bouton J H, Latch G C M, Hill N S, Hoveland C S, McCann M A, Watson R H, Parish J A, Hawkins L L, Thompson F N: Reinfection of tall fescue cultivars with non-ergot alkaloid-producing endophytes. *Agron J* 2002, 94:567-574.
13. Florea S, Andreeva K, Machado C, Mirabito P M, Schardl C L: Elimination of marker genes from transformed filamentous fungi by unselected transient transfection with a Cre-expressing plasmid. *Fungal Genet Biol* 2009, 46:721-730.
14. Schardl C L, Young C A, Hesse U, Amyotte S G, Andreeva K, Calie P J, Fleetwood D J, Haws D C, Moore N, Oeser B, Panaccione D G, Schweri K K, Voisey C R, Farman M L, Jaromczyk J W, Roe B A, O'Sullivan D M, Scott B, Tudzynski P, An Z, Arnaoudova E G, Bullock C T, Charlton N D, Chen L, Cox M, Dinkins R D, Florea S, Glenn A E, Gordon A, Güldener U, Harris D R, Hollin W, Jaromczyk J, Johnson R D, Khan A K, Leistner E, Leuchtmann A, Li C, Liu J, Liu J, Liu M, Mace W, Machado C, Nagabhyru P, Pan J, Schmid J, Sugawara K, Steiner U, Takach J, Tanaka E, Webb J S, Wilson E V, Wiseman J L, Yoshida R, Zeng Z: Plant-symbiotic fungi as chemical engineers: multi-genome analysis of the Clavicipitaceae reveals dynamics of alkaloid loci. *PLoS Genet* 2013, 9:e1003323.
15. Nicholson M J, Koulman A, Monahan B J, Pritchard B L, Payne G A, Scott B: Identification of two aflatrem biosynthetic gene loci in *Aspergillus flavus* and metabolic engineering in *Penicillium paxilli* to elucidate gene function. *Appl Environ Microbiol* 2009, 75:7469-7481.
16. Smith C A, Woloshuk C P, Robertson D, Payne G A: Silencing of the aflatoxin gene cluster in a diploid strain of *Aspergillus flavus* is suppressed by ectopic aflR expression. *Genetics* 2007, 176:2077-2086.

17. Qi X, Li Y, Honda S, Hoffmann S, Marz M, Mosig A, Podlevsky J D, Stadler P F, Selker E U, Chen J J-L: The common ancestral core of vertebrate and fungal telomerase RNAs. *Nucl Acids Res* 2013, 41:450-462.
18. Reeck G R, de Haën C, Teller D C, Doolittle R F, Fitch W M, Dickerson R E, Chambon P, McLachlan A D, Margoliash E, Jukes T H, Zuckerkandl E: "Homology" in proteins and nucleic acids: a terminology muddle and a way out of it. *Cell* 1987, 50:667.
19. Schardl C L, Young C A, Pan J, Florea S, Takach J E, Panaccione D G, Farman M L, Webb J S, Jaromczyk J, Charlton N D, Nagabhyru P, Chen L, Shi C, Leuchtmann A: Currencies of mutualisms: sources of alkaloid genes in vertically transmitted epichloae. *Toxins (Basel)* 2013, 5:1064-1088.
20. Ryan K L, Akhmedov N G, Panaccione D G: Identification and structural elucidation of ergotryptamine, a new ergot alkaloid produced by genetically modified *Aspergillus nidulans* and natural isolates of *Epichloë* species. *J Agric Food Chem* 2015, 63:61-67.
21. Ekanayake P N, Hand M L, Spangenberg G C, Forster J W, Guthridge K M: Genetic diversity and host specificity of fungal endophyte taxa in fescue pasture grasses. *Crop Sci* 2012, 52:2243-2252.
22. Takach J E, Young C A: Alkaloid genotype diversity of tall fescue endophytes. *Crop Sci* 2014, 54:667-678.
23. Young C A, Charlton N D, Takach J E, Swoboda G A, Trammell M A, Huhman D V, Hopkins A A: Characterization of *Epichloë coenophiala* within the US: are all tall fescue endophytes created equal? *Frontiers in chemistry* 2014, 2:95. doi: 10.3389/fchem.2014.00095.
24. Panaccione D G, Johnson R D, Wang J H, Young C A, Damrongkool P, Scott B, Schardl C L: Elimination of ergovaline from a grass-*Neotyphodium* endophyte symbiosis by genetic modification of the endophyte. *Proc Natl Acad Sci USA* 2001, 98:12820-12825.
25. Panaccione D G, Tapper B A, Lane G A, Davies E, Fraser K: Biochemical outcome of blocking the ergot alkaloid pathway of a grass endophyte. *J Agric Food Chem* 2003, 51:6429-6437.
26. Ryan K L, Moore C T, Panaccione D G: Partial reconstruction of the ergot alkaloid pathway by heterologous gene expression in *Aspergillus nidulans*. *Toxins (Basel)* 2013, 5:445-455.
27. Watanabe H, Somei M, Sekihara S-i, Nakagawa K, Yamada F: Dopamine receptor stimulating effects of chanoclavine analogues, tricyclic ergot alkaloids, in the brain. *The Japanese Journal of Pharmacology* 1987, 45:501-506.
28. Cassady J M, Li G S, Spitzner E B, Floss H G, Clemens J A: Ergot alkaloids. Ergolines and related compounds as inhibitors of prolactin release. *Journal of Medicinal Chemistry* 1974, 17:300-307.
29. Tsai H F, Siegel M R, Schardl C L: Transformation of *Acremonium coenophialum*, a protective fungal symbiont of the grass *Festuca arundinacea*. *Curr Genet* 1992, 22:399-406.
30. Florea S, Schardl C L, Hollin W: Detection and isolation of *Epichloë* species, fungal endophytes of grasses. *Current Protocols in Microbiology* 2015, 38:19A.11.11-19A.11.24.
31. Latch G C M, Christensen M J: Artificial infections of grasses with endophytes. *Ann Appl Biol* 1985, 107:17-24.
32. Chung K R, Hollin W, Siegel M R, Schardl C L: Genetics of host specificity in *Epichloë typhina*. *Phytopathology* 1997, 87:599-605.
33. An Z-q, Siegel M R, Hollin W, Tsai H-F, Schmidt D, Schardl C L: Relationships among non-*Acremonium* sp. fungal endophytes in five grass species. *Appl Environ Microbiol* 1993, 59:1540-1548.
34. Pan J, Bhardwaj M, Nagabhyru P, Grossman R B, Schardl C L: Enzymes from fungal and plant origin required for chemical diversification of insecticidal loline alkaloids in grass-*Epichloë* symbiota. *PLoS ONE* 2014, 9:e115590. doi: 115510.111371/journal.pone.0115590.
35. Spiering M J, Faulkner J R, Zhang D-X, Machado C, Grossman R B, Schardl C L: Role of the LolP cytochrome P450 monooxygenase in loline alkaloid biosynthesis. *Fungal Genet Biol* 2008, 45:1307-1314.
36. Panaccione D G, Ryan K L, Schardl C L, Florea S: Analysis and modification of ergot alkaloid profiles in fungi. *Meth Enzymol* 2012, 515:267-290.
37. Spiering M J, Davies E, Tapper B A, Schmid J, Lane G A: Simplified extraction of ergovaline and peramine for analysis of tissue distribution in endophyte-infected grass tillers. *J Agric Food Chem* 2002, 50:5856-5862.
38. Blankenship J D, Spiering M J, Wilkinson H H, Fannin F F, Bush L P, Schardl C L: Production of loline alkaloids by the grass endophyte, *Neotyphodium uncinatum*, in defined media. *Phytochemistry* 2001, 58:395-401.
39. Livak K J, Schmittgen T D: Analysis of relative gene expression data using real-time quantitative PCR and the $2^{-\Delta\Delta CT}$ method. *Methods* 2001, 25:402-408.
40. Ehrlich K C: Non-aflatoxigenic *Aspergillus flavus* to prevent aflatoxin contamination in crops: advantages and limitations. *Front Microbiol* 2014, 5:50. doi 10.3389/fmicb.2014.00050.
41. Florea, S, Phillips, T D, Panaccione, D G, Farman, M L, Schardl, C L: Chromosome-End Knockoff Strategy to Reshape Alkaloid Profiles of a Fungal Endophyte. G3 2016, 6: 8, doi: 10.1534/g3.116.029686.

```
SEQUENCE LISTING:
SEQ ID NO: 1: e7480 contig_32884 length = 181
TAACCCTAACCCTAACCCTAAGCTCGAGGCCATGATGGCCTTTAAAGTCT

ACGTACTCACTAGTTAAGAAGCGCTTACGCCGTTCCACTTGTGCCTTTGA

CTGGATGATGGATACAGATAGTAACTAACCGTGGACAGTATGATATTATT

ATGCACGTGGATTCCAAACAACAATGTTACC

SEQ ID NO: 2: e7479 contig40627 length = 228
ACCCTAACCCTAACCCTAACCCTAACCCTAACCCTAACCCTAACCCTAAC

CCTAACCCTAACCCTAACCCTAACCCTAACCCTAACCCTAACCCTAACCC

TAACCCTAAGCTCGAGGCCATGATGGCCTTTAAAGTCTACGTACTCACTA

GTTAAGAAGCGCTTACGCCGTTCCACTTGTGCCTTTGACTGGATGATGGA

TACAGATAGTAACTAACCGTGGACAGTA

SEQ ID NO: 3 lpsA1 gene fragment used in pKAE329
TAAGAAGCGCTTACGCCGTTCCACTTGTGCCTTTGACTGGATGATGGATA

CAGATAGTAACTAACCGTGGACAGTATGATATTATTATGCACGTGGATTC

CAAACAACAATGTTACCTCTCGTATTGGGACTATTTTCTATCGGATGAAC

AGGCAAACCACCTTGCCGGTGCGCTGAATGTTGCCATGATATCCATTTTC

GAGTCACCACACCGGCCCGTAGGACAGGTAGAGTTGTTCAGCTACCTCGA

CCAGCAGAAACTGCTGCAGTGGAGCGGACAGGCACCCATTGCATCCGAGT

CTTGTATTGGCGATCTAATCGGCCAGAATTGCCACTCGCGACCTGATTCT
```

CTTGCTGTAGACTCCTGGGACGGTTCCTTTACCTACCAAGAGCTCGATCG
CCTTTCATCCACTCTTGCCAACAAACTTCGTGCGGCGGGCGTGGGACCGG
AAGTTTTTGTCACCGCGTGCTTTGATCGTTGTAAGTGGATGCCGGTTGCT
ATGCTAGGCATTATCAAAGCCGGCGGCGCCATCTGTGCTCTTGACCCTTC
ATACCCTCTCGGCCGCCTAACCGGGATGTGTCAATTGTTAAAATCGACCG
TTGTATTGACTACGGCAAATAATGCCCAGCAGGCAGAGCAATTGGAACTT
ACCACAATTATCCTCGGTAGTGATCTATGGACAGGCGATAGTTATGACGA
ACAGGAACGACAAGCACCTTTGTCCAATGTATGCCCCAGCAATGCATTGT
ATGCAGTCTTCACTTCAGGTTCCACTGGGAAGCCGAAAGGGGTCGTGGTT
GAACATCGATCATTCTCTTCATGCGCTCTAGCATCACTGAAACCCCTGGA
TATCCGGCCACACGACCGCGTACTGCATTTTTCATCATATGCGTTCGATA
TCAGCATATTTGAAACCCTCGCAACCCTGACTGCAGGGGCTTCCGTAGCA
ATCCCATCTGAAAAGGCCCGCAGAGAGGATCTGCCTGGCGCCATGAGAGA
GCTACAGGCGACGTGGGCTTTCCTTACACCCACGGTAGCCCGCATGTATC
AACCAGAGGACTTTCCTTCGCTCAGGACTTTGTGTTTAGGGGCGAGGCC
ATCCATACTTCAGATATCGGGCTGTGGGCGTCGAAGAATCTAATCACAGG
ATATAATCCCGCGGAATCTTGCCCGCTCGGGATCTCCGGCCTAGCTGATC
AGTCTGCGGCCAGTTTTCTGGGGTGGTCTTTTTCGTCCCAGGCCTCCTGG
ATCGTGGACCCTCGAGACTACCAGAAGCTGGCCCCTATTGGCGCAGTAGG
AGAACTTTTGATCGAAGGACCAACCGTAGCAAGGGGTTATATCGACGACC
TAACATGCTCTCATCCTGACTCGCCATTCGTTCTCTCTCCTCCACAATGG
TTGTCCCGTTTCCGTTCAAGCACTTCTCAAGATACACGTCTGTATCGAAC
GGGTGATCTGGTACAGTATGGCAGTAATGGATCCGTGCACTTTATCGGCC
GGAAAGATCTCCAGGTAAAGGTACACGGGCAGAGAGTGGAGCTGTCTGAG
ATTGAATTCCAGCTCCACAAGACTTTACTTCCTTTGGATTGCAAGGTGGT
CGTCGACGCGGTGACTTTCACAGGTCATACCTCTATAATCGCATTTATTA
CCGCTGCAGAGCATTCAGACTTGGAAAACGAAGACGACGCCGACCGGTCA
CCGGACGTGAAAGTAATCACCCAAGATTTCGAGATCCAAGCCGCCGATGC
AGCAACCAAGTTACAGAGCATTCTTCCGAAACACATGGTTCCAACCTATA
TTTACCTGTGGGACATATTCCCATGTCTAGGAGCGGAAAGGTTGATCGA
AAGAAATTAAGATCCCTGGCCATCTCGCTACCCCGAGAGACTCTATATTG
CATCGGGCGGCAGCCAGGTCCGGGGAAATAGTGGCAACCGATGTTGAGC
GTCGTCTACAACTCCTCTTTGCTCACGTATTGGATCTTTCTCCCGAGAAA
ATCAAGGCGGACAGCGATTTCTTCCGCCTAGGTGGAGATTCTATCTATGC
GATGAAGCTTTTAGCGTTAGCTCCTCAACAGGGGCTACGTCATCTCACAT
ACGAGGAAATTTTTCGCCATCCGAAATTGAGGGATCTGGCCGCAGCATCA
AGTTCATTATCCAACATTTCTTCAGAAATTCCGGAAGACCTTGGACCGGC
ACCCTTCAGTCTGGCGCGGGATGCAGACTCGCTCACGAAAATCGCAAGTG
AGCAGTGTGGTGTCGCTGTAGGAGACATTGAGGATATTTATCCTTGTACC
AGTCTACAGGAGAGTCTCATCGCATCTACTGCCCGTGACCAAGATGCGTA
CGTAGGGGTGCAATCCTTTACTCTCAATGAAGATATTGATACAACCCGGC

TAAAAATGGCTTGGAAAATGACCTCTGCCGGCCATCCGATTCTTCGCACG
CGCATCATTCAGACGGACAGCGGTACACCTTACCAGGCCGTTATAAGAGG
GCCGCTCTCCTGGTCGGAGGAAAGCAGCAGCGAGGACCTCCCTCCCCAGT
TCAAGCCCTCTATTGGTCTGGGGACCCCATTAGTCCAGCTGTGCCTCACC
AAAAGTCGGTTACTTGTTGCCATGCACCACGCACTGTACGACGGTTGGTC
GTTGCCATTGCTGCTCGTGGAAGTTGATCAGGCATATCGCCAGCTCTTTG
TGCGGCAGCTGCCGCCGTTCAACCGGTATGTGAAGCATGTAACGGAAACC
GTGGACTCTGCGGCCTCATTTTGGAAAGCAGAGTTACAGGACGTGGATCC
TGTACACTTCCCGCCGCTGCCTCATCTCAATTATAAGCCAGAGCCTCGCG
CATTACTCACAAAGTTAATTACCGTTACTGCCCACACCAATGCACAACAC
AACGTGACGGTTGCAACCGAGATACAACTAGCCTGGGCCCTCACCAGTCA
CACTTATACTAACAGCCAAGACGTGGTTTTCGGAATCATCTCCTCGGGAC
GCGGTGCGCCAGTCGCGGGCATTGAGAGGATGTTAGGCCCTACCTTTGCG
AGTACGCCGCTCCGAGTGCCCATTGATCCGGCCCAGGAGGTGAGAGAAGC
TCTGGAAGAGTTGCAATACCGGCTCGCGGAGCAAACGAAGTATGTGCAAA
CTGGCTTGCAGCGAATTCGCCAACAGGGGCCAAATGCAGCGGCAGCTTGC
AGCTTCCAAACAATGCTTGTCGTGGAGCCCAACCAACCATTCAAGACTCA
GAGTGCTTGGTTCAGCCGACACGAGTTTTTGTCCGAGCTCACAAGATTTA
GCAGCCATTCTCTGACACTCAGGTGCAAGTTGCTAGCCAGATCAGTCGAA
GTCACTGCGATTTACGACCAGTTGGTTGTACCCGACGCTCAGATGCAACG
TATCTTATCCCAATTCCAACACATTTTAACACAGATCCAGGGCATTGGAT
CCCGAAACACCACTATTGGAGACATTAATAGGCTAAGCCCCGGAGACTGG
AACGAGCTTCAGGCATGGAATTCTACATTGCCTCCAGTGCTGGAGCTGTG
TGTGCACCAGATGATTCAAGCGAAAGCCCAAATGCAACCGGAGGCGTTGG
CAATTCATTCGTGGGATGGTGCCCTGACGTACAAGGAGCTTGAGGACTAC
GCCAAAGGACTTGCCCACCGCCTCCACGCCCTTGGTGTCAGGCCAAATAC
CTTCGTTGCCATCTATCTGCAGAAGTCTTTGTGGGTAGTGGTGGCCCAGC
TTGCTGTGCTCATGGCGGGTGCTGCTTTTACAACGTTGGAGACCTCTCAA
CCCATCAACCGTCTACGCGACGTCTGTCGTACCGTCCAACCCACCGTGGT
ATTGACATCTGACGAGTTGCGGTTATCTGGTGCAGACCTTGAAGTACCGG
CTCCCCTTCTAGTGATCAATCTGCAGCTTCTCCTTCAAGAGTCCGGTAGC
CACAGCCAGCCTTTCGAGAACCACACCATGACGGCCTCCGATGCCATGTA
CAGCATTGCCACATCCGGCACCACTGGTAAACCCAAGGTGGTGGTCATCG
AGCATCAAGCGTTTCTAGCCAACTCGAGACACCTGATTGATCGCTGGGGG
TTCACTGCAGACTCTCGTGTCCTTCAATTTGCCGGATACAGCTTCGATGC
AATGATTGTGGAGCATTTCATTACTCTTCTTGCGGGCGGCTGCATCTGCA
TTCCTTCCTCATTTGACCGGGACAACCGTCTAGCGACGTGTATTGCCGAG
ATGCGCGTCAACTGGGCGATGTTGACGTCTTCAGTTATCCCGCTGCTCAC
CCCTGCTACTGTGCCGACCCTGCAAACGCTGGTACAGGCCGGCGAACCCA
TGCATCAAGGCATAACTGACTGCTGGGCTTCTCATGTGCGATTGTTCAAC

-continued

```
GCCTACGGCCCAACGGAGTGCAGCGTGATCAGTACCACCAGCAACGTCAT
CAATCCAGATGCCAGGAACGCAAGGAATATTGGTTTCACGACAGGTGGCG
TCTGCTGGATTGTCGACCCCGAGCATCCAGAGAGCCCACCCGTTCCCATC
GGGGCTGAGGGTGAACTAATCATTGAGGGCGCTATTCTCGCTCGGGCTA
TCTAGGCGACCGTGTACGAACTGCTGCAGCTTTCACTCCCCGTCCTGGCT
GGTTGGATGATTTCAGAGGCAGTAGCGGAGATAATCGAGTTTACCGGACT
GGCGACATTGTCAGATACGATCCAGACGGATCCATCTCCTATGTGCGGCG
CAAGGATTCCCAGGTCAAGCTCCGCGGCCAGCGAGTAGAGCTGCTGGATG
TCGAGCACCATCTCCAGAACTGCTTTCCGGGCGCGCTTCAGGTTGTCGCT
GATATTGTTACTGTGCCCAATACTCGGTCGAGCGCCCTGGTGGCCCTTGT
ATTAGCCACTCCCACTTCCTCTTCGAGCGCGGCAATCGAATCGTGTCCAA
TTGATGACCAAGCAATGACGGCCCATGGCCTCTTGTTACTCGCTAACAAC
CCCCAGTTCCTCATTGACGCAAGCGCTGCCGAGCTCGCACTCCAGGACCG
AGTTCCCTCGTATATGGTGCCTAGTTTGATCATACCTACCTCACACTTTC
CACGGGACGTCAGCGGAAAGGTCAACCGTGGAGAGATAAGCCGGTCTCTC
GCAGCTCTTTCTCGGCAAGAGTGGGATGGATATGTTTCCACGAACAGAGT
CGCTCCGACTAGCGGTCTCGAACGTGAACTGCAGAAGATCTGGGCCCTCA
TTCTGAATATCCCTCCTGATACCATTGGCGTCCATGACAGCTTCTTCCGA
CTGGGGGGTGACTCGATCACCTGTATGCAGGTTGCTGCACAGTGTAGTAG
AACAGGAATCCCGATTACTGTTAAGGATGTCTTCAAGCGACGGACAATTG
AGGAGCTAGCGGCCGCAGCAGTGGTGGTACAGTGTCCTGAATCATCTACA
ACAGAGCTTGTCAACACCGCAGAAGCCAAATTCTCCTTTTATGGCCCCGG
ACAACTGGAGGAGTATATGATGCAGATCCAACCCCAGCTCGGAGAAGGCC
AGATCGTAGAGGACATCTATCCGTGCTCTCCAATCCAGCGGGGATTCTC
ATGAGCCACGCCCGTAACTCCAGCAATTACGAAGAAGTTATTCAGTGGAA
GGTCATCAGCAGAGCCCCGGTCAACGTCTATCGTCTGCGTGATGCCTGGG
CCCAGGTGGTAGATCGGCACGCGGTTCTTCGTACTTTGTTCTTGCATGTT
TGTGAGGAAAACTATTTGGATCAAGTAGTGCTGAGGAGCCATTCACCAAT
GGTCCTGGTATACAACGAAGGGGAGGAGCCAGTTAATCCGGTATCAACTG
GCTGCTCTCAGCCTATGCATCATCTCCGAGTCAAGCGATCGAGTACGGGC
GAGATTACCGTTCGTTTGCATATCAACCACGCACTTGTCGATGGGACCTC
CTTGTTCATCATCAGACGGGAGTTGGCCATGGCCTACGAAGGTCGTCTAG
CCTCATCTCGTGCATCATCACCCTACCGGGACTACATTGCATACTTGCAA
AACTGCCATGCACAAATACAGTCAAAGGAGTACTGGAAGTCGTACATGGA
GGGCACAGCACCTTGTCTATTCCCTTCTCTGAAGAACGCGGGCGCACAAG
ATTCACAACAGCCTTTTGAGGCTTTCAAGCTGCAACTGGGAGCAACTGCT
GACCTGAATCAATTCTGCGAGAATCACCGATTGGCACTTACCAGTGTACT
CCACGTGGTGTGGGCTATGGTGGTCCAACGCTACACGGCAATGGACGAGG
TCTGCTTTGGCTATATGACTTCTGGTCGCCATGTGCCCGTGGCTGGCGTT
CAAGATATCGTAGGCCCGTTGTTCAACATGCTGGTGGCGCGGGTGGGCTT
GCCGCATGATGCCACGCTGCTCTCTGTCATGCAGAAGTATCATGACAACT
```

```
TCCTGATCAGTCTCGACCATCAGCACCAGTCCTTAGCCGAAACACTGCAT
TCCGTCGGGTCGGCTTCGGGGGAGTTATTCAACACGCTGGTTTCAATATT
CAATGATCAGCGAGAGGGGGAGCCGGCCCATAAGTCGTCTGCCGTCACTC
TGGTGGGTGATGACATACATAGCCGATCGGAGGTAGGTGCTGTCTTACTC
GCCTTATCGTCTTGCCCCATATTGAGTTCATTGCTAACCAAACACTTCCA
CCACAGTACGCCATCACATTAAACGTTCTCATGCTCGCGGACCAGGTTCA
TATGCAGCTCTCTTATCACACATCATTGCTGAGTGATAATTATGCCAGGA
TGATTGCTAAAACCTTCCGCCATGTCCTGGCCACAGTCCTAGGACAACCT
CAGCTCCGTCTCAATGAGATCGAGATGCTGGATGAGGAACATAGAAGCGG
CCTCTACGAGCGGAATCATGCGATCGTGCCTTCATACGACAGCT
```

SEQ ID NO: 4 the 45-bp synthetic "oligotag"
derived from polylinkerDdeI and polylinkerSpeI
5'-

TAAGCTCGAGGCCATGATGGCCTTTAAAGTCTACGTACTCACTAG-3'

SEQ ID NO: 5
GGGACTAGTTAAGAAGCGCTTACGCCGTTCC

SEQ ID NO: 6
CACACGCGTAGCTGTCGTATGAAGGCACGAT

SEQ ID NO: 7
/5'
Phos/TAAGCTCGAGGCCATGATGGCCCTTTAAAGTCTACGTACTCA

SEQ ID NO: 8
/5'
Phos/CTAGTGAGTACGTAGACTTTAAAGGCCATCATGGCCTCGAGC

SEQ ID NO: 9
AGAAACAGACAGGGCTATTC

SEQ ID NO: 10
CTCGCCGGCATGCGTCAAAA

SEQ ID NO: 11
TTATTGGATGAAACCTTAGCTAGTTGG

SEQ ID NO: 12
CTCGCCGGCATGCGTCAAAT

SEQ ID NO: 13
CACTTTAAACCTAATGCACTACACTAAGACCCC

SEQ ID NO: 14
AATCTGGCCAACATGGTTCCCATG

SEQ ID NO: 15
GCTTGACAAACGCACCAAGTTATCG

SEQ ID NO: 16
TGTACACCACTTCAACGAGGCTTG

SEQ ID NO: 17
CGAAGTTATCTCGACGGTATCG

SEQ ID NO: 18
TCGGCGAGTACTTCTACACA

SEQ ID NO: 19
TCCTTGCCACCAAGGCAGATTG

SEQ ID NO: 20
ACATTGTCCACGGCAAGCCCTC

SEQ ID NO: 21
CGTGCGGATAATGAAGGCGTCC

SEQ ID NO: 22
CGATGAGAAATCCATTGGCACCG

SEQ ID NO: 23
GGCATGGCAGTCAAGTTCTTCAC

SEQ ID NO: 24
ACATTGGCTGTCCAAGTAGGGT

SEQ ID NO: 25
CCCAGAACTTTCGTCATGTCCG

SEQ ID NO: 26
ATCCCGTCCAGTGGCGGAAGTA

SEQ ID NO: 27
TTGCCAAGACTCTCCATGAGAT

SEQ ID NO: 28
ACCACGTCGGTCTTAATACAGCG

SEQ ID NO: 29
GATGGCCTTTAAAGTCTACGTACTC

SEQ ID NO: 30
ATATCATGGCAACATTCAGCGCAC

SEQ ID NO: 31 telomere repeat that can be
repeated about 3 to about 26 times
CCCTAA SEQ ID NO: 32 telomere repeat that can be
repeated about 3 to about 26 times
CCCTAATGTTCA SEQ ID NO: 33 telomere repeat that can be
repeated about 3 to about 26 times
CCCTAAC SEQ ID NO: 34 telomere repeat that can be
repeated about 3 to about 26 times
CTAACC SEQ ID NO: 35 telomere repeat that can be
repeated about 3 to about 26 times
TAACCC SEQ ID NO: 36 telomere repeat that can be
repeated about 3 to about 26 times
AACCCT SEQ ID NO: 37 telomere repeat that can be
repeated about 3 to about 26 times
ACCCTA SEQ ID NO: 38 telomere repeat that can be
repeated about 3 to about 26 times
TAAGGG SEQ ID NO: 39 telomere repeat that can be
repeated about 3 to about 26 times
AAGGGT SEQ ID NO: 40 telomere repeat that can be
repeated about 3 to about 26 times
AGGGTA SEQ ID NO: 41 telomere repeat that can be
repeated about 3 to about 26 times
GGGTAA SEQ ID NO: 42 telomere repeat that can be
repeated about 3 to about 26 times
GGTAAG SEQ ID NO: 43 telomere repeat that can be
repeated about 3 to about 26 times
GTAAGG SEQ ID NO: 44 telomere repeat that can be
repeated about 3 to about 26 times
CCTAATGTTCAC SEQ ID NO: 45 telomere repeat that can be
repeated about 3 to about 26 times
CTAATGTTCACC SEQ ID NO: 46 telomere repeat that can be
repeated about 3 to about 26 times
TAATGTTCACCC SEQ ID NO: 47 telomere repeat that can be
repeated about 3 to about 26 times
AATGTTCACCCT SEQ ID NO: 48 telomere repeat that can be
repeated about 3 to about 26 times
ATGTTCACCCTA SEQ ID NO: 49 telomere repeat that can be
repeated about 3 to about 26 times
TGTTCACCCTAA SEQ ID NO: 50 telomere repeat that can be
repeated about 3 to about 26 times
GTTCACCCTAAT SEQ ID NO: 51 telomere repeat that can be
repeated about 3 to about 26 times
TTCACCCTAATG SEQ ID NO: 52 telomere repeat that can be
repeated about 3 to about 26 times
TCACCCTAATGT SEQ ID NO: 53 telomere repeat that can be
repeated about 3 to about 26 times
CACCCTAATGTT SEQ ID NO: 54 telomere repeat that can be
repeated about 3 to about 26 times
ACCCTAATGTTC SEQ ID NO: 55 telomere repeat array of the
scaffold of the e19 assembly downstream of
lpsB1
CCCTAACCCTAACCCTAACCCTAACCCTAT

---

We claim:

1. A fungus strain comprising an at least 80% deletion of an ergot alkaloid gene, wherein said strain is selected from the group consisting of e7479 deposited under ATCC Accession No. PTA-126678 and e7480 deposited under ATCC Accession No. PTA-126679.

2. A fungus strain comprising SEQ ID NO: 1 or SEQ ID NO: 2.

3. The fungus strain of claim 2, wherein the fungus strain is *Epichloe coenophiala*.

4. A composition comprising the fungus strain of claim 1 or 2 and a grass selected from the group consisting of a fescue grass or a perennial ryegrass.

* * * * *

SEQUENCE LISTING

<160> NUMBER OF SEQ ID NOS: 55

<210> SEQ ID NO 1
<211> LENGTH: 181
<212> TYPE: DNA
<213> ORGANISM: Artificial Sequence
<220> FEATURE:
<223> OTHER INFORMATION: recombination sequence

<400> SEQUENCE: 1

| | |
|---|---|
| taaccctaac cctaacccta agctcgaggc catgatggcc tttaaagtct acgtactcac | 60 |
| tagttaagaa gcgcttacgc cgttccactt gtgcctttga ctggatgatg gatacagata | 120 |
| gtaactaacc gtggacagta tgatattatt atgcacgtgg attccaaaca acaatgttac | 180 |
| c | 181 |

<210> SEQ ID NO 2
<211> LENGTH: 228
<212> TYPE: DNA
<213> ORGANISM: Artificial Sequence
<220> FEATURE:
<223> OTHER INFORMATION: recombination sequence

<400> SEQUENCE: 2

| | |
|---|---|
| accctaaccc taaccctaac cctaacccta accctaaccc taaccctaac cctaaccctaa | 60 |
| accctaaccc taaccctaac cctaaccctaa accctaaccc taaccctaag ctcgaggcca | 120 |
| tgatggcctt taaagtctac gtactcacta gttaagaagc gcttacgccg ttccacttgt | 180 |
| gcctttgact ggatgatgga tacagatagt aactaaccgt ggacagta | 228 |

<210> SEQ ID NO 3
<211> LENGTH: 6944
<212> TYPE: DNA
<213> ORGANISM: Artificial Sequence
<220> FEATURE:
<223> OTHER INFORMATION: recombination sequence

<400> SEQUENCE: 3

| | |
|---|---|
| taagaagcgc ttacgccgtt ccacttgtgc ctttgactgg atgatggata cagatagtaa | 60 |
| ctaaccgtgg acagtatgat attattatgc acgtggattc caaacaacaa tgttacctct | 120 |
| cgtattggga ctattttcta tcggatgaac aggcaaacca ccttgccggt gcgctgaatg | 180 |
| ttgccatgat atccattttc gagtcaccac accggcccgt aggacaggta gagttgttca | 240 |
| gctacctcga ccagcagaaa ctgctgcagt ggagcggaca ggcacccatt gcatccgagt | 300 |
| cttgtattgg cgatctaatc ggccagaatt gccactcgcg acctgattct cttgctgtag | 360 |
| actcctggga cggttccttt acctaccaag agctcgatcg cctttcatcc actcttgcca | 420 |
| acaaacttcg tgcggcgggc gtgggaccgg aagttttgt caccgcgtgc tttgatcgtt | 480 |
| gtaagtggat gccggttgct atgctaggca ttatcaaagc cggcggcgcc atctgtgctc | 540 |
| ttgaccctc atacctctc ggccgcctaa ccgggatgtg tcaattgtta aaatcgaccg | 600 |
| ttgtattgac tacggcaaat aatgcccagc aggcagagca attggaactt accacaatta | 660 |
| tcctcggtag tgatctatgg acaggcgata gttatgacga acaggaacga caagcacctt | 720 |
| tgtccaatgt atgccccagc aatgcattgt atgcagtctt cacttcaggt tccactggga | 780 |
| agccgaaagg ggtcgtggtt gaacatcgat cattctcttc atgcgctcta gcatcactga | 840 |
| aaccccctgga tatccggcca cacgaccgcg tactgcattt ttcatcatat gcgttcgata | 900 |
| tcagcatatt tgaaaccctc gcaaccctga ctgcagggc ttccgtagca atcccatctg | 960 |
| aaaaggcccg cagagaggat ctgcctggcg ccatgagaga gctacaggcg acgtgggctt | 1020 |
| tccttacacc cacggtagcc cgcatgtatc aaccagagga ctttccttcg ctcaggactt | 1080 |
| tgtgtttagg gggcgaggcc atccatactt cagatatcgg gctgtgggcg tcgaagaatc | 1140 |
| taatcacagg atataatccc gcggaatctt gcccgctcgg gatctccggc ctagctgatc | 1200 |
| agtctgcggc cagttttctg gggtggtctt tttcgtccca ggcctcctgg atcgtggacc | 1260 |

```
ctcgagacta ccagaagctg gccectattg gegcagtagg agaactttg atcgaaggac      1320
caaccgtagc aagggttat atcgacgacc taacatgctc tcatcctgac tcgccattcg      1380
ttctctctcc tccacaatgg ttgtcccgtt tccgttcaag cacttctcaa gatacacgtc     1440
tgtatcgaac gggtgatctg gtacagtatg gcagtaatgg atccgtgcac tttatcggcc     1500
ggaaagatct ccaggtaaag gtacacgggc agagagtgga gctgtctgag attgaattcc     1560
agctccacaa gactttactt cctttggatt gcaaggtggt cgtcgacgcg gtgactttca     1620
caggtcatac ctctataatc gcatttatta ccgctgcaga gcattcagac ttggaaaacg     1680
aagacgacgc cgaccggtca ccggacgtga aagtaatcac ccaagatttc gagatccaag     1740
ccgccgatgc agcaaccaag ttacagagca ttcttccgaa acacatggtt ccaaccatat     1800
atttacctgt gggacatatt cccatgtcta ggagcgaaaa ggttgatcga agaaattaa      1860
gatccctggc catctcgcta ccccgagaga ctctatattg catcgggcgg cagccaggtc     1920
cgggggaaat agtggcaacc gatgttgagc gtcgtctaca actcctcttt gctcacgtat     1980
tggatctttc tcccgagaaa atcaaggcgg acagcgattt cttccgccta ggtggagatt     2040
ctatctatgc gatgaagctt ttagcgttag ctcctcaaca ggggctacgt catctcacat     2100
acgaggaaat ttttcgccat ccgaaattga gggatctggc cgcagcatca agttcattat     2160
ccaacatttc ttcagaaatt ccggaagacc ttggaccggc accttcagt ctggcgcggg      2220
atgcagactg gctcacgaaa atcgcaagtg agcagtgtgg tgtcgctgta ggagacattg     2280
aggatattta tccttgtacc agtctacagg agagtctcat cgcatctact gcccgtgacc     2340
aagatgcgta cgtaggggtg caatccttta ctctcaatga agatattgat acaacccggc     2400
taaaaatggc ttggaaaatg acctctgccg gccatccgat tcttcgcacg cgcatcattc     2460
agacggacag cggtacacct taccaggccg ttataagagg gccgctctcc tggtcggagg     2520
aaagcagcag cgaggacctc cctccccagt tcaagccctc tattggtctg ggacccccat     2580
tagtccagct gtgcctcacc aaaagtcggt tacttgttgc catgcaccac gcactgtacg     2640
acggttggtc gttgccattg ctgctcgtgg aagttgatca ggcatatcgc cagctctttg     2700
tgcggcagct gccgccgttc aaccggtatg tgaagcatgt aacggaaacc gtggactctg     2760
cggcctcatt ttggaaagca gagttacagg acgtggatcc tgtacacttc ccgccgctgc     2820
ctcatctcaa ttataagcca gagcctcgcg cattactcac aaagttaatt accgttactg     2880
cccacaccaa tgcacaacac aacgtgacgg ttgcaaccga gatacaacta gcctgggccc     2940
tcaccagtca cacttatact aacagccaag acgtggtttt cggaatcatc tcctcgggac     3000
gcggtgcgcc agtcgcgggc attgagagga tgttaggccc tacctttgcg agtacgccgc     3060
tccgagtgcc cattgatccg gcccaggagg tgagagaagc tctggaagag ttgcaatacc     3120
ggctcgcgga gcaaacgaag tatgtgcaaa ctggcttgca gcgaattcgc caacaggggc     3180
caaatgcagc ggcagcttgc agcttccaaa caatgcttgt cgtggagccc aaccaaccat     3240
tcaagactca gagtgcttgg ttcagccgac acgagttttt gtccgagctc acaagattta     3300
gcagccattc tctgacactc aggtgcaagt tgctagccag atcagtcgaa gtcactgcga     3360
tttacgacca gttggttgta cccgacgctc agatgcaacg tatcttatcc caattccaac     3420
acattttaac acagatccag ggcattggat cccgaaacac cactattgga gacattaata     3480
ggctaagccc cggagactgg aacgagcttg aggcatggaa ttctacattg cctccagtgc     3540
tggagctgtg tgtgcaccag atgattcaag cgaaagccca aatgcaaccg gaggcgttgg     3600
caattcattc gtgggatggt gccctgacgt acaaggagct tgaggactac gccaaaggac     3660
```

```
ttgcccaccg cctccacgcc cttggtgtca ggccaaatac cttcgttgcc atctatctgc   3720
agaagtcttt gtgggtagtg gtggcccagc ttgctgtgct catggcgggt gctgctttta   3780
caacgttgga gacctctcaa cccatcaacc gtctacgcga cgtctgtcgt accgtccaac   3840
ccaccgtggt attgacatct gacgagttgc ggttatctgg tgcagacctt gaagtaccgg   3900
ctcccctttct agtgatcaat ctgcagcttc tccttcaaga gtccggtagc cacagccagc   3960
ctttcgagaa ccacaccatg acggcctccg atgccatgta cagcattgcc acatccggca   4020
ccactggtaa acccaaggtg gtggtcatcg agcatcaagc gtttctagcc aactcgagac   4080
acctgattga tcgctggggg ttcactgcag actctcgtgt ccttcaattt gccggataca   4140
gcttcgatgc aatgattgtg gagcatttca ttactcttct tgcgggcggc tgcatctgca   4200
ttccttcctc atttgaccgg gacaaccgtc tagcgacgtg tattgccgag atgcgcgtca   4260
actgggcgat gttgacgtct tcagttatcc cgctgctcac ccctgctact gtgccgaccc   4320
tgcaaacgct ggtacaggcc ggcgaaccca tgcatcaagg cataactgac tgctgggctt   4380
ctcatgtgcg attgttcaac gcctacggcc caacggagtg cagcgtgatc agtaccacca   4440
gcaacgtcat caatccagat gccaggaacg caaggaatat tggtttcacg acaggtggcg   4500
tctgctggat tgtcgacccc gagcatccag agagcccacc cgttcccatc ggggctgagg   4560
gtgaactaat cattgagggc gctattctcg ctcggggcta tctaggcgac cgtgtacgaa   4620
ctgctgcagc tttcactccc cgtcctggct ggttggatga tttcagaggc agtagcggag   4680
ataatcgagt ttaccggact ggcgacattg tcagatacga tccagacgga tccatctcct   4740
atgtgcggcg caaggattcc caggtcaagc tccgcggcca gcgagtagag ctgctggatg   4800
tcgagcacca tctccagaac tgctttccgg gcgcgcttca ggttgtcgct gatattgtta   4860
ctgtgcccaa tactcggtcg agcgccctgg tggcccttgt attagccact cccacttcct   4920
cttcgagcgc ggcaatcgaa tcgtgtccaa ttgatgacca agcaatgacg gcccatggcc   4980
tcttgttact cgctaacaac ccccagttcc tcattgacgc aagcgctgcc gagctcgcac   5040
tccaggaccg agttccctcg tatatggtgc ctagtttgat catacctacc tcacactttc   5100
cacgggacgt cagcggaaag gtcaaccgtg gagagataag ccggtctctc gcagctcttt   5160
ctcggcaaga gtgggatgga tatgtttcca cgaacagagt cgctccgact agcggtctcg   5220
aacgtgaact gcagaagatc tgggccctca ttctgaatat ccctcctgat accattggcg   5280
tccatgacag cttcttccga ctgggggtg actcgatcac ctgtatgcag gttgctgcac   5340
agtgtagtag aacaggaatc ccgattactg ttaaggatgt cttcaagcga cggacaattg   5400
aggagctagc ggccgcagca gtggtggtac agtgtcctga atcatctaca acagagcttg   5460
tcaacaccgc agaagccaaa ttctcctttt atggccccgg acaactggag gagtatatga   5520
tgcagatcca accccagctc ggagaaggcc agatcgtaga ggacatctat ccgtgctctc   5580
caatccagcg ggggattctc atgagccacg cccgtaactc cagcaattac gaagaagtta   5640
ttcagtggaa ggtcatcagc agagccccgg tcaacgtcta tcgtctgcgt gatgcctggg   5700
cccaggtggt agatcggcac gcggttcttc gtactttgtt cttgcatgtt tgtgaggaaa   5760
actatttgga tcaagtagtg ctgaggagcc attccaccaat ggtcctggta tacaacgaag   5820
gggaggagcc agttaatccg gtatcaactg gctgctctca gcctatgcat catctccgag   5880
tcaagcgatc gagtacgggc gagattaccg ttcgtttgca tatcaaccac gcacttgtcg   5940
atgggacctc cttgttcatc atcagacggg agttggccat ggcctacgaa ggtcgtctag   6000
```

```
cctcatctcg tgcatcatca ccctaccggg actacattgc atacttgcaa aactgccatg    6060
cacaaataca gtcaaaggag tactggaagt cgtacatgga gggcacagca ccttgtctat    6120
tcccttctct gaagaacgcg ggcgcacaag attcacaaca gccttttgag gctttcaagc    6180
tgcaactggg agcaactgct gacctgaatc aattctgcga gaatcaccga ttggcactta    6240
ccagtgtact ccacgtggtg tgggctatgg tggtccaacg ctacacggca atggacgagg    6300
tctgctttgg ctatatgact tctggtcgcc atgtgcccgt ggctggcgtt caagatatcg    6360
taggcccgtt gttcaacatg ctggtggcgc gggtgggctt gccgcatgat gccacgctgc    6420
tctctgtcat gcagaagtat catgacaact tcctgatcag tctcgaccat cagcaccagt    6480
ccttagccga aacactgcat tccgtcgggt cggcttcggg ggagttattc aacacgctgg    6540
tttcaatatt caatgatcag cgagaggggg agccggccca taagtcgtct gccgtcactc    6600
tggtgggtga tgacatacat agccgatcgg aggtaggtgc tgtcttactc gccttatcgt    6660
cttgccccat attgagttca ttgctaacca aacacttcca ccacagtacg ccatcacatt    6720
aaacgttctc atgctcgcgg accaggttca tatgcagctc tcttatcaca catcattgct    6780
gagtgataat tatgccagga tgattgctaa aaccttccgc catgtcctgg ccacagtcct    6840
aggacaacct cagctccgtc tcaatgagat cgagatgctg gatgaggaac atagaagcgg    6900
cctctacgag cggaatcatg cgatcgtgcc ttcatacgac agct                     6944
```

```
<210> SEQ ID NO 4
<211> LENGTH: 45
<212> TYPE: DNA
<213> ORGANISM: Artificial Sequence
<220> FEATURE:
<223> OTHER INFORMATION: primer

<400> SEQUENCE: 4
taagctcgag gccatgatgg cctttaaagt ctacgtactc actag                   45

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
gggactagtt aagaagcgct tacgccgttc c                                  31

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
cacacgcgta gctgtcgtat gaaggcacga t                                  31

<210> SEQ ID NO 7
<211> LENGTH: 41
<212> TYPE: DNA
<213> ORGANISM: Artificial Sequence
<220> FEATURE:
<223> OTHER INFORMATION: primer

<400> SEQUENCE: 7
taagctcgag gccatgatgg cctttaaagt ctacgtactc a                       41
```

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
ctagtgagta cgtagacttt aaaggccatc atggcctcga gc                          42

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agaaacagac agggctattc                                                   20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctcgccggca tgcgtcaaaa                                                   20

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
ttattggatg aaaccttagc tagttgg                                           27

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctcgccggca tgcgtcaaat                                                   20

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
cactttaaac ctaatgcact acactaagac ccc                                    33

<210> SEQ ID NO 14
<211> LENGTH: 24
<212> TYPE: DNA
<213> ORGANISM: Artificial Sequence
<220> FEATURE:

<223> OTHER INFORMATION: primer

<400> SEQUENCE: 14
aatctggcca acatggttcc catg                                          24

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
gcttgacaaa cgcaccaagt tatcg                                         25

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
tgtacaccac ttcaacgagg cttg                                          24

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
cgaagttatc tcgacggtat cg                                            22

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tcggcgagta cttctacaca                                               20

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
tccttgccac caaggcagat tg                                            22

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
acattgtcca cggcaagccc tc                                            22

```
<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
cgtgcggata atgaaggcgt cc                                              22

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
cgatgagaaa tccattggca ccg                                             23

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
ggcatggcag tcaagttctt cac                                             23

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
acattggctg tccaagtagg gt                                              22

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
cccagaactt tcgtcatgtc cg                                              22

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
atcccgtcca gtggcggaag ta                                              22

<210> SEQ ID NO 27
<211> LENGTH: 22
<212> TYPE: DNA
<213> ORGANISM: Artificial Sequence
<220> FEATURE:
<223> OTHER INFORMATION: primer
```

```
<400> SEQUENCE: 27
ttgccaagac tctccatgag at                                              22

<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
accacgtcgg tcttaataca gcg                                             23

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
gatggccttt aaagtctacg tactc                                           25

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30
atatcatggc aacattcagc gcac                                            24

<210> SEQ ID NO 31
<211> LENGTH: 6
<212> TYPE: DNA
<213> ORGANISM: Homo sapiens

<400> SEQUENCE: 31 ccctaa                                                                 6

<210> SEQ ID NO 32
<211> LENGTH: 12
<212> TYPE: DNA
<213> ORGANISM: Homo sapiens

<400> SEQUENCE: 32
ccctaatgtt ca                                                         12

<210> SEQ ID NO 33
<211> LENGTH: 7
<212> TYPE: DNA
<213> ORGANISM: Homo sapiens

<400> SEQUENCE: 33 ccctaac                                                                7

<210> SEQ ID NO 34
<211> LENGTH: 6
<212> TYPE: DNA
<213> ORGANISM: Homo sapiens

<400> SEQUENCE: 34 ctaacc                                                                 6
```

```
<210> SEQ ID NO 35
<211> LENGTH: 6
<212> TYPE: DNA
<213> ORGANISM: Homo sapiens

<400> SEQUENCE: 35 taaccc                                                                 6

<210> SEQ ID NO 36
<211> LENGTH: 6
<212> TYPE: DNA
<213> ORGANISM: Homo sapiens

<400> SEQUENCE: 36 aaccct                                                                 6

<210> SEQ ID NO 37
<211> LENGTH: 6
<212> TYPE: DNA
<213> ORGANISM: Homo sapiens

<400> SEQUENCE: 37 acccta                                                                 6

<210> SEQ ID NO 38
<211> LENGTH: 6
<212> TYPE: DNA
<213> ORGANISM: Homo sapiens

<400> SEQUENCE: 38 taaggg                                                                 6

<210> SEQ ID NO 39
<211> LENGTH: 6
<212> TYPE: DNA
<213> ORGANISM: Homo sapiens

<400> SEQUENCE: 39 aagggt                                                                 6

<210> SEQ ID NO 40
<211> LENGTH: 6
<212> TYPE: DNA
<213> ORGANISM: Homo sapiens

<400> SEQUENCE: 40 agggta                                                                 6

<210> SEQ ID NO 41
<211> LENGTH: 6
<212> TYPE: DNA
<213> ORGANISM: Homo sapiens

<400> SEQUENCE: 41 gggtaa                                                                 6

<210> SEQ ID NO 42
<211> LENGTH: 6
<212> TYPE: DNA
<213> ORGANISM: Homo sapiens

<400> SEQUENCE: 42
```

-continued

```
ggtaag                                                                    6

<210> SEQ ID NO 43
<211> LENGTH: 6
<212> TYPE: DNA
<213> ORGANISM: Homo sapiens

<400> SEQUENCE: 43 gtaagg                                                                    6

<210> SEQ ID NO 44
<211> LENGTH: 12
<212> TYPE: DNA
<213> ORGANISM: Homo sapiens

<400> SEQUENCE: 44
cctaatgttc ac                                                            12

<210> SEQ ID NO 45
<211> LENGTH: 12
<212> TYPE: DNA
<213> ORGANISM: Homo sapiens

<400> SEQUENCE: 45
ctaatgttca cc                                                            12

<210> SEQ ID NO 46
<211> LENGTH: 12
<212> TYPE: DNA
<213> ORGANISM: Homo sapiens

<400> SEQUENCE: 46
taatgttcac cc                                                            12

<210> SEQ ID NO 47
<211> LENGTH: 12
<212> TYPE: DNA
<213> ORGANISM: Homo sapiens

<400> SEQUENCE: 47
aatgttcacc ct                                                            12

<210> SEQ ID NO 48
<211> LENGTH: 12
<212> TYPE: DNA
<213> ORGANISM: Homo sapiens

<400> SEQUENCE: 48
atgttcaccc ta                                                            12

<210> SEQ ID NO 49
<211> LENGTH: 12
<212> TYPE: DNA
<213> ORGANISM: Homo sapiens

<400> SEQUENCE: 49
tgttcaccct aa                                                            12

<210> SEQ ID NO 50
<211> LENGTH: 12
<212> TYPE: DNA
<213> ORGANISM: Homo sapiens

<400> SEQUENCE: 50
```

```
gttcaccta at                                                    12

<210> SEQ ID NO 51
<211> LENGTH: 12
<212> TYPE: DNA
<213> ORGANISM: Homo sapiens

<400> SEQUENCE: 51
ttcaccctaa tg                                                   12

<210> SEQ ID NO 52
<211> LENGTH: 12
<212> TYPE: DNA
<213> ORGANISM: Homo sapiens

<400> SEQUENCE: 52
tcaccctaat gt                                                   12

<210> SEQ ID NO 53
<211> LENGTH: 12
<212> TYPE: DNA
<213> ORGANISM: Homo sapiens

<400> SEQUENCE: 53
caccctaatg tt                                                   12

<210> SEQ ID NO 54
<211> LENGTH: 12
<212> TYPE: DNA
<213> ORGANISM: Homo sapiens

<400> SEQUENCE: 54
accctaatgt tc                                                   12

<210> SEQ ID NO 55
<211> LENGTH: 36
<212> TYPE: DNA
<213> ORGANISM: Homo sapiens

<400> SEQUENCE: 55
ccctaaccct aaccctaacc ctaaccctaa ccctat                         36
```